(12) United States Patent
El-Nokaly et al.

(10) Patent No.: US 7,213,600 B2
(45) Date of Patent: May 8, 2007

(54) METHOD AND APPARATUS FOR MEASURING ACUTE STRESS

(75) Inventors: Magda El-Nokaly, Cincinnati, OH (US); Michael Lee Hilton, Fairfield, OH (US); Kevin Lee Doyle, Fairfield, OH (US); Daniel Raymond Schaiper, Hamilton, OH (US); Abel Saud, Loveland, OH (US); Diane Lynn Prickel, Batesville, IN (US)

(73) Assignee: The Procter & Gamble Company, Cincinnati, OH (US)

( * ) Notice: Subject to any disclaimer, the term of this patent is extended or adjusted under 35 U.S.C. 154(b) by 790 days.

(21) Appl. No.: 10/405,378

(22) Filed: Apr. 2, 2003

(65) Prior Publication Data

US 2003/0236451 A1 Dec. 25, 2003

Related U.S. Application Data

(60) Provisional application No. 60/369,678, filed on Apr. 3, 2002.

(51) Int. Cl.
*A61B 19/00* (2006.01)
(52) U.S. Cl. .................................. 128/898; 600/26
(58) Field of Classification Search ........ 128/897–898; 600/26–28, 300–301
See application file for complete search history.

(56) References Cited

U.S. PATENT DOCUMENTS 6,102,847 A 8/2000 Stielau

FOREIGN PATENT DOCUMENTS

CA 1276888 11/1990
JP HEI 11(1999)-19076 1/1999

OTHER PUBLICATIONS

Kirschbaum, Clemens, et al., "Salivary Cortisol in Psychobiological Research: An Overview," Biological Psychology/Pharmacopsychology, Neuropsychobiology 1989:22:150-169.
Heuberger, Eva, et al., "Effects of Chiral Fragrances on Human Autonomic Nervous System Parameters and Self-evaluation", Chem. Senses 26:281-292, 2001.

(Continued)

*Primary Examiner*—John P. Lacyk
(74) *Attorney, Agent, or Firm*—James Derry; Leonard W. Lewis

(57) ABSTRACT

A method and apparatus are provided to quantify psychological and physiological components to measure acute stress in humans, in which a stimulus can be applied to the test subject's environment during the test. The method involves multiple stress/relaxation intervals while physiological measurements are taken and "measured," and involves questionnaires that are answered after each of the intervals to "measure" the test subject's psychological state. A computerized testing apparatus acquires the physiological measurements, and also is used by the test subject in answering the questionnaires. The "stimulus" can be a fragrance, flavor, product, or task, and a "blank stimulus" is normally used during one of the stress intervals.

16 Claims, 13 Drawing Sheets

OTHER PUBLICATIONS

Vernet-Maury, Evelyne, et al., "Basic emotions induced by odorants: a new approach based on autonomic pattern results," Journal of the Autonomic Nervous System, vol. 75, 1999, pp. 176-183.

Diego, Miguel A., et al., "Aromatherapy Positively Affects Moods, EEG Patterns of Alertness and Math Conputations," International Journal of Neuroscience, vol. 96, 1998, pp. 217-224.

Friedlander, L., et al., "Testing the alexithymia hypothesis: physiological and subjective responses during relaxation and stress," *The Journal of Nervous and Mental Disease*, vol. 185, No. 4, Apr. 1997, pp. 233-239.

Wilken, J. A., et al., "Trait anxiety and prior exposure to non-stressful stimuli: effects on psychophysiological arousal and anxiety," *International Journal of Psychophysiology*, vol. 37, No. 3, Sep. 2000, pp. 233-242.

METHOD AND APPARATUS FOR MEASURING ACUTE STRESS

CROSS REFERENCE TO RELATED APPLICATIONS

This application claims the benefit of U.S. Provisional Application No. 60/369,678, filed Apr. 3, 2002.

TECHNICAL FIELD

The present invention relates generally to stress measurement methodologies and is particularly directed to a Stress Measurement Protocol (SMP) of the type which quantitatively measures the physiological and psychological effects of aromas, products, and tasks (or other influences) on acute stress. The invention is specifically disclosed as a computerized testing apparatus that measures a person's physiological parameters related to acute stress, and operates with a methodology that simultaneously provides a measurement of the person's psychological reactions to acute stress.

BACKGROUND OF THE INVENTION

Stress has been, and still is, a difficult thing to measure. One difficulty in measuring stress comes directly from the lack of a concise definition for stress. One definition of stress is: "Stress is the non specific response of the body to any demand." (Hans Selye, "Stress without Distress," published by Philadelphia: Lippincott, 1974.) Another difficulty in measuring stress is in its diagnoses. Stress reveals itself by a constellation of common symptoms with varying degrees of specificity. Stress is difficult to diagnose because it reveals itself by a constellation of common symptoms with varying degrees of specificity. The patterns are a function of: the stimulus (demand or pressure), their build up, as well as the individual organism predisposition (weak links).

Examples of common "weak links" and the symptoms of their malfunction are as follows: (1) brain overstress: fatigue, aches and pains, crying spells, depression, anxiety attacks, insomnia, brain shrinkage; (2) gastrointestinal tract: ulcer, cramps and diarrhea, colitis, IBS, thyroid gland malfunction; (3) others: itchy skin rashes, decrease resistance to infections, high blood pressure, heart attack, stroke, etc.

Another difficulty is the complexity of the human stress response. To measure stress, "mind and body" both have to be taken into consideration, as there is no psychological event without a resulting somatic (bodily) event and vice versa. Stress has both psychological and physiological components; measuring only one component is insufficient to provide a complete understanding. Stress response varies greatly between individuals. One person, for instance, may display large changes in electrodermal activity with increased stress and show only moderate changes in heart rate and peripheral blood flow volume, while another individual may show the reverse pattern.

FIG. 1, based on work by Dr. George Everly (as modified by one of the present inventors), shows a model of the human stress response that provides a framework for understanding the places in the stress response that are amenable to measures. The stress response begins with a stressor event setting into motion a cascade of biological processes which gets interpreted by the brain. This interpretation is influenced by a variety of physical, psychological, and social factors. Once the event occurs the cognitive/affective domain is the critical "causal" phase in most stress responses. Cognitive appraisal is how a person perceives the stress which, like beauty, appears to in the eye of the beholder. Affective integration is the effect of the emotional well-being. Both are influenced by biological predispositions, personality patterns, learning history, and resources.

If the event is perceived as a threat, the body begins the stress response which proceeds through three stages:

(1) Neural: There is an immediate activation of the sympathetic nervous system, which results in reduced peripheral blood flow, accelerated heartbeats, dilated pupils, thickened saliva, and several other physiological changes.

(2) Neuroendocrine: There is a near immediate effect of releasing hormones, such as epinephrine (adrenaline) and norepinephrine (noradrenaline), that will activate the endocrine system and kick in the "fight or flight" response.

(3) Endocrine: The endocrine glands release a flood of powerful stress hormones such as ACTH and cortisol that cause a prolonged stress reaction.

All of the above results in some form of coping behavior. Certain forms of "treatment" for stress have been practiced or theorized in the past. Psychotherapy has been used for more adaptive health promoting cognitive/affective style. Another manner of treatment has used certain types of products, such as: techniques, games, or conditioning the mind and reducing stress-arousing thoughts such as "mind chatter", bad memories or anticipations. Other forms of therapy have included: music or aromatherapy (reported to trigger memory and mood change), which are known to direct thoughts so as to produce peace and tranquility.

Aromatherapy has existed as folklore for centuries, but there has been very little rigorous scientific investigation of aromatheraputic effects on human psychology and physiology. There are many scientific, social, and economic reasons for this. Some of the scientific difficulties in measuring aromatheraputic effects are as follows:

(1) Aromatheraputic claims tend to be broad and ill-defined, using somewhat ambiguous words like soothing, harmonizing, happiness, sensuality, well being, etc. (2) Stress is also somewhat ambiguous and ill-defined. There is no standard definition of stress and, consequently, there are no widely accepted standards for measuring stress. One reason for this is that every person's psychological and physiological response to stress is different and can change over time. (3) The magnitude of aromatheraputic effects is probably small, making them difficult to isolate. (4) The mind-body connection is particularly strong here. There is much scientific evidence that a person's physiological reaction to an odorant may depend on their psychological response to the odorant, i.e., whether or not the person likes the odor. (5) Animal studies by Buchbauer indicate that only specific varieties of essential oils—indeed, in some cases only specific enantiomers of fragrance molecules—produce an aromatheraputic effect. This could explain some of the contradictory findings in the scientific literature regarding aromatherapy. A generic lavender, for instance, might not contain the correct amounts, proportions, or chemical species of the various components which are needed to produce an effect.

Some patent literature in the prior art has dealt with stress measurements: a method for measuring "Antistress Effects of Fragrances" was disclosed in KOKAI Patent Application No. HE11 (1991) 19076, by Pola Chemical Industry, Inc. A psychological stress was applied in the presence of a fragrance, and a saliva sample was collected before and after the exposure. The concentration of the adrenocorticol hormones in the saliva was determined. Unfortunately, this methodology is rather invasive (as would be blood or urine samples), and is not desirable as it increases the test subject's stress and adds complexity to the measurements. The adrenocorticol hormones are released in a secondary step, and have a short life in acute stress, and further may not get released in sufficient amounts to be measured. They are very difficult to measure in acute stress due to their short half-life.

In another patent document, by Warren et. al EP 0183436 B2 (1991) stress was measured by systolic blood pressure and a self administered questionnaire, in which respondents indicated their degree of relaxation, anger, anxiety, happiness, tenseness, embarrassment, calmness, fear, and sleepiness on a 7-point scale. A number of active odorants was found to significantly have an effect on the above human parameters when administered either alone or incorporated into a complex fragrance. These findings paralleled the measurements on systolic blood pressure taken in the same experiment. However, one measurement is not determinative, and no one has found a relation between most of the above basic emotions and blood pressure.

One of the failings of the majority of previous "stress-measuring" methodologies is that only one type of stress component was being evaluated: either physiological attributes or psychological attributes, but not both. One exception to this was disclosed in a paper published by the Oxford University Press in 2001, titled, "Effects of Chiral Fragrances on Human Autonomic Nervous System Parameters and Self-evaluation," by Eva Heuberger, et al. However, even this paper did not provide a methodology for measuring the effects of fragrances in both "stress" and "relaxation" cycles.

Another paper titled, "Basic emotions induced by odorants: a new approach based on autonomic pattern results," by Vernet-Maury, et al., appearing in the Journal of the Autonomic Nervous System, Volume 75, 1999, pages 176–183, is an example of prior art that uses multiple physiological measurements. However, Vernet-Maury, et al. do not use these measurements to measure stress; instead, the measurements are used in an attempt to classify a subject's response to an odorant to one of the basic emotions (i.e., happiness, surprise, sadness, fear, disgust, or anger). This paper does not provide a methodology for evaluating stress, and also does not use odorants in "stress" and "relaxation" cycles.

Yet another paper titled, "Aromatherapy Positively Affects Mood, EEG Patterns of Alertness and Math Computations," by Diego, et al., appearing in the International Journal of Neuroscience, Volume 96, 1998, pages 217–224, describes an experiment using EEG sensors to monitor the brainwaves of subjects before, during, and after aromatherapy is administered. In this paper, quick answer questionnaires are administered to ascertain the effect of odorants on mood and anxiety of subjects. The methodology described in this paper does not evaluate the effects of odorants during stress, and does not utilize "stress" and "relaxation" cycles.

SUMMARY OF THE INVENTION

Accordingly, it is an advantage of the present invention to provide a methodology and apparatus for testing and evaluating acute stress levels of human test subjects by acquiring both physiological and psychological information during alternating periods of stress and relaxation.

It is another advantage of the present invention to provide a methodology and apparatus for testing and evaluating acute stress levels of human test subjects using both physiological and psychological information while subjecting the test subjects to a stimulus, such as a fragrance, flavor, or product, or while the test subjects are performing an activity or task.

It is a further advantage of the present invention to provide methodology and apparatus for testing and evaluating acute stress levels of human test subjects by acquiring physiological data from biosensors, such as EKG and blood volume pulse (BVP) sensors, and by acquiring psychological data from questionnaires.

Additional advantages and other novel features of the invention will be set forth in part in the description that follows and in part will become apparent to those skilled in the art upon examination of the following or may be learned with the practice of the invention.

To achieve the foregoing and other advantages, and in accordance with one aspect of the present invention, a method for evaluating acute stress of a person is provided, in which the method comprises the steps of: (a) providing a computerized apparatus having a memory circuit for storage of data, an interface circuit, a processing circuit, and at least one sensing device that is in communication with the interface circuit, wherein the at least one sensing device is used to detect at least one physiological parameter of a test subject; (b) initiating a first stress interval, during which the test subject performs at least one predetermined task designed to induce some acute stress; (c) initiating a first questionnaire interval, during which the test subject answers questions designed to evaluate at least one psychological component of acute stress; (d) initiating a first relaxation interval, during which the test subject is allowed to relax; (e) initiating a second questionnaire interval, during which the test subject answers questions designed to evaluate at least one psychological component of acute stress; (f) initiating a second stress interval, during which the test subject performs at least one predetermined task designed to induce some acute stress; and (g) initiating a third questionnaire interval, during which the test subject answers questions designed to evaluate at least one psychological component of acute stress; and wherein a stimulus may be introduced into the test subject's environment during at least one of: (i) the first stress interval, (ii) the first relaxation interval, and (iii) the second stress interval.

In accordance with another aspect of the present invention, a testing apparatus is provided, which comprises: a memory circuit for storage of data; at least one sensing device used to detect at least one physiological parameter of a test subject; an interface circuit that is in communication with the at least one sensing device; and a processing circuit that is configured to control the flow of data between the memory circuit and the interface circuit, and in which the processing circuit is configured to: (a) monitor the at least one physiological parameter during at least one stress interval; (b) monitor the at least one physiological parameter during at least one relaxation interval; and (c) introduce a stimulus into the test subject's environment during one of: (i) the at least one stress interval, and (ii) the at least one relaxation interval.

Still other advantages of the present invention will become apparent to those skilled in this art from the following description and drawings wherein there is described and shown a preferred embodiment of this invention in one of the best modes contemplated for carrying out the invention. As will be realized, the invention is capable of other different embodiments, and its several details are capable of modification in various, obvious aspects all without departing from the invention. Accordingly, the drawings and descrippions will be regarded as illustrative in nature and not as restrictive.

All documents cited are, in relevant part, incorporated herein by reference; the citation of any document is not to be construed as an admission that it is prior art with respect to the present invention.

BRIEF DESCRIPTION OF THE DRAWINGS

The accompanying drawings incorporated in and forming a part of the specification illustrate several aspects of the present invention, and together with the description and claims serve to explain the principles of the invention. In the drawings:

DETAILED DESCRIPTION OF THE INVENTION

Reference will now be made in detail to the present preferred embodiment of the invention, an example of which is illustrated in the accompanying drawings, wherein like numerals indicate the same elements throughout the views.

Figure 2:
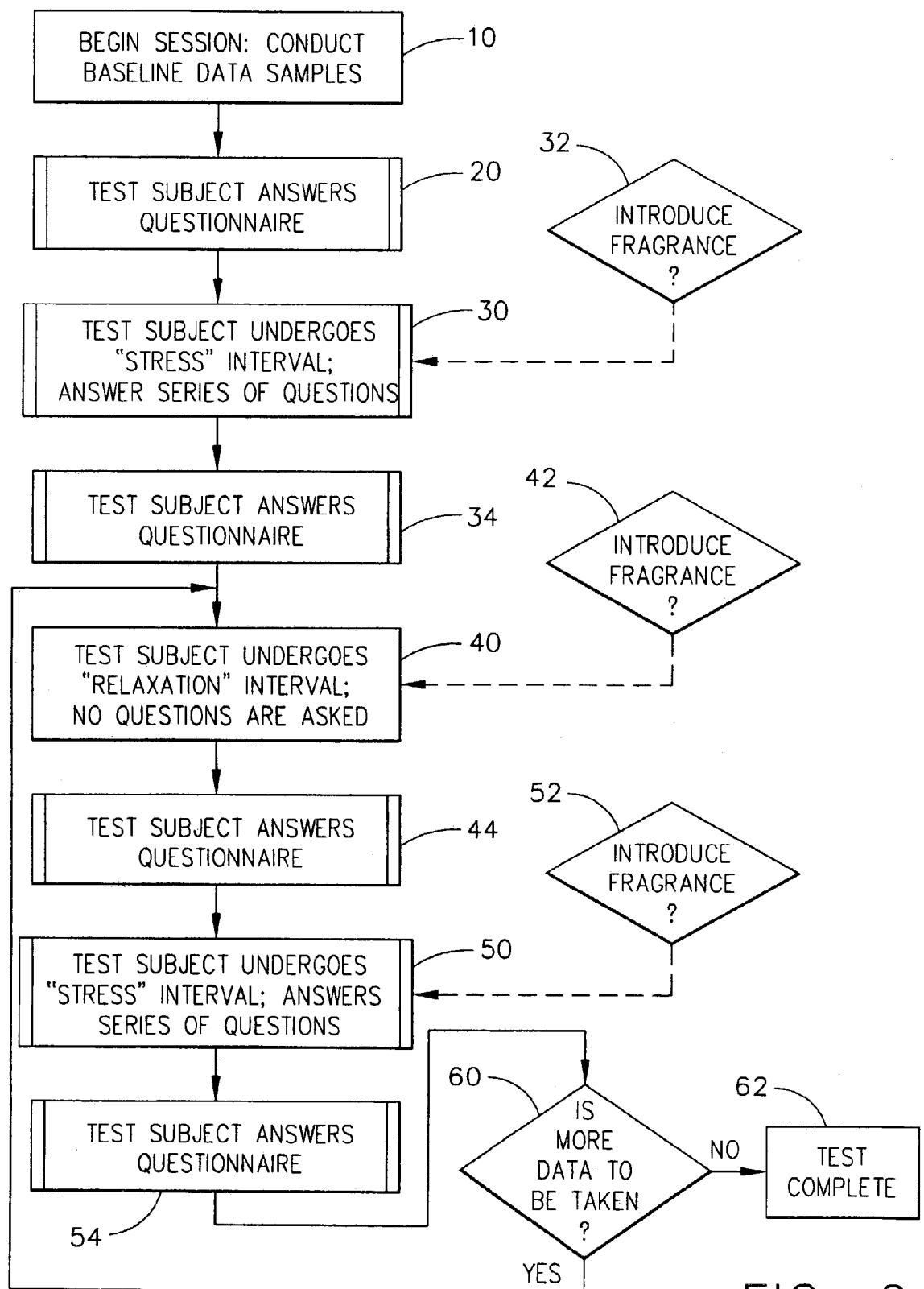
FIG. 2 is a flow chart of some of the significant steps performed in an acute stress testing procedure, as according to the principles of the present invention.
Figure 3:
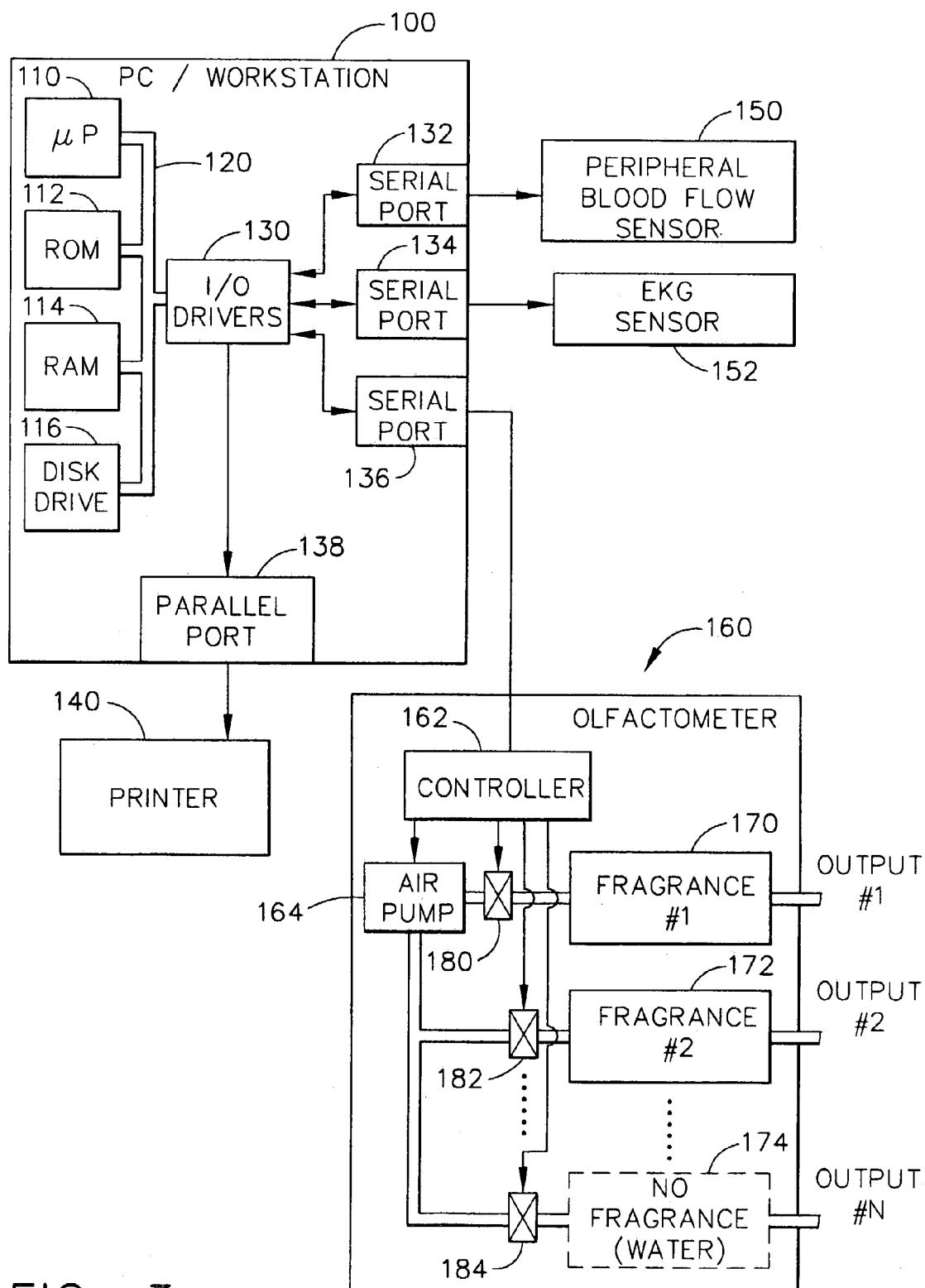
FIG. 3 is a block diagram of the major hardware components of a testing computer, used in the testing procedure of FIG. 2.

As noted above, the present invention involves an Aromatherapy Stress Measurement Protocol (SMP) which quantitatively measures the physiological and psychological effects of fragrances (or other influences) on acute stress. Referring now to FIGS. 2–3, a testing setup is used for testing in this example at least one fragrance and a "blank." In certain tests described herein, three fragrances will be used along with the blank. In general, the fragrances are in liquid form, and are dispensed by air movement over the liquid to create a gaseous mixture. The blank could consist of water, or plain air, or perhaps no air movement at all.

It should be noted that, for the purposes of this description of the present invention, the term "fragrance" represents a type of "stimulus" that could either be relaxing or stimulating, or perhaps could have a neutral effect on a person. Moreover, the terms "fragrance" or "stimulus" can be interchanged in most cases, with respect to the principles of the present invention. Furthermore, the term "fragrance" can literally represent an actual fragrance (e.g., in a liquid state) or an odor (e.g., in a gaseous state), or the term "fragrance" can represent a flavor (such as in a beverage). The term "fragrance" can also represent essential oils, an aroma or scent. A "fragrance" can be subliminal (at a concentration too low to be consciously detected by a human) or non-subliminal (at a concentration high enough to be consciously detected by a human). Finally, the terms "fragrance" or "stimulus" can alternatively represent some type of "product" or could represent a "task." In the case of a "product," the terms fragrance/stimulus could represent a perfume or a cologne, for example, or some other complex formulation (e.g., a mixture of two or more perfumes); or some type of therapeutic device or medical device, for example, such as hot towels, or chemically-activated heat-releasing wraps such as those under the registered trademark THERMACARE®, owned by The Procter & Gamble Company. In the case of a "task," the terms fragrance/stimulus could represent some activity that may be relaxing, such as a person taking a hot shower, or cleaning, or washing dishes or clothing, ironing, or performing some other ergonometrically-designed tasks to relieve stress. Further details of some of these examples are discussed below.

Physiological measurements of sympathetic nervous system activation are made using an instrument package called ProComp+™ (manufactured by Thought Technologies, Ltd., of West Chazy, N.Y.), which is attached to a computer 100 (e.g., a PC or workstation). Psychological measurements are made using a chronic stress questionnaire administered at the beginning of the experiment (see step 20 on FIG. 2 and step 212 on FIG. 4), and an acute stress self-report that is administered several times during the course of the experiment (see steps 34, 44, and 54 on FIG. 2, and steps 222, 226, 232, 236, 242, 246, 252, and 256 on FIG. 4).

A general methodology of such a test, according to the principles of the present invention, will be described in reference to FIG. 2, after which an exemplary hardware configuration will be described in some detail in reference to FIG. 3. A more detailed description of a specific test setup and procedure will then be provided after these somewhat general descriptions for FIGS. 2 and 3.

Referring now to FIG. 2, the first step at reference numeral 10 begins the test session, and the initial step is to conduct baseline data samples. As will be discussed below in greater detail, the test subject is connected to certain biosensors, while the experimenter or "user" checks the instrumentation to be certain that "good" signals are being received by a test computer 100 (see FIG. 3). The next step at 20 can be used to have the test subject answer a chronic stress questionnaire, which will also be discussed in greater detail below, in reference to Tables #3 and #4.

Now starting at a step 30, the test subject undergoes a series of "stress" intervals and "relaxation" intervals, as needed to provide the test results desired by the user. The first such stress interval occurs at step 30, in which the test subject undergoes some relatively mild acute stress (as opposed to chronic stress) by answering a series of questions. This is similar to a step 220 on FIG. 4, which illustrates a series of "stress" and "relax" intervals or "stages" of a test that involves three or four odors/fragrances. It will be understood that, while the illustrated embodiment of FIG. 2 uses a period of questions and oral answers to cause some acute stress in the test subject, other methodologies could be used instead, such as having the subject watch stressful film clips or video clips, or to perform some other task or activity that may tend to introduce a measure of acute stress.

On FIG. 2, step 30 is the first instance on the flow chart of FIG. 2 in which a fragrance can be introduced, at a decision step 32. The only decision in step 32 is as to what type of fragrance will be introduced. In some test subjects, there will be no fragrance at all, or the "fragrance" will be water that has no odor. If the water sample is used for the "fragrance," then this is considered to be a "blank," as noted above.

During step 30, the test subject has both psychological and physiological data ascertained from the testing computer 100. (A second computer could be used for the psychological data, if desired, but is not necessary.) The types of data taken by the physiological sensors in conjunction with computer 100 are described in greater detail below. Further data (the psychological data) is also taken by the test subject's computer 100, in which the test subject is asked to perform certain tasks that will subject the test subject to a certain amount of acute stress. As discussed below in greater detail, the test subject is asked to perform a certain amount of oral arithmetic, and then uses the test subject's computer for a "reaction time drill" and an "attention task," which also introduce some acute stress.

Once the stress interval 30 has been completed, the test subject answers a questionnaire at a step 34. This questionnaire is designed to measure acute stress and, according to the current preferred embodiment, uses a "mood adjective checklist" (see Table #5 below) that describes a person's moods or feelings, and also asks the test subject to answer four other "new" questions that relate to physical symptoms that people often associate with stress. These four questions are described below, after the description of Table #5.

After the test subject finishes answering the questionnaire in step 34, the testing procedure moves to a step 40 in which the test subject undergoes a "relaxation" interval, during which no questions are asked. Moreover, the test subject is instructed to relax in whatever fashion best suited for the person that is being tested. A fragrance can be introduced during step 40, as indicated on FIG. 2 at a decision step 42. This introduction of a fragrance at this point is not necessarily useful, since data taken by the present inventors up to this time have preliminarily indicated that any type of effect of a fragrance to potentially more relax a person will not be easily noticeable during the relaxation interval 40. More precisely, the individual responses of individual human beings during a relaxation interval are much more varied, and therefore, any relaxation attributes of a fragrance or other type of stimulus introduced in step 42 may not be measurable or noticeable from one test subject to the next. It appears that any type of relaxation effect will be more noticeable during a "stress" interval, such as the previously performed step 30, by introduction of a fragrance at step 32.

Once the relaxation interval 40 has run for a predetermined time interval, the test subject again answers a questionnaire at a step 44. In the current preferred embodiment, the questionnaire at 44 is identical to the questionnaire used at step 34. These questionnaires are intended to provide a measure of the test subject's psychological state from the acute stress of interval 30, or after the relaxation interval 40. The measure of the subject's psychological state can be affected by a fragrance introduced at step 32 or at step 42 (if step 42 is used).

Once the test subject finishes the questionnaire at step 44, the test subject now undergoes a new "stress" interval at a step 50, and again answers a series of questions. The current preferred embodiment uses the same types of questions at step 50 as were used at step 30, and the biosensors are again used to measure the physiological state of the test subject under acute stress that the test subject incurs from answering the questions. A fragrance can be introduced at a decision step 52 at this time, if desired. Again, the fragrance could be water, or plain air, which would be a blank. Of course, if a blank fragrance was introduced at step 32, then for most experiments at step 52 an actual fragrance that is to be evaluated would be introduced; or vice versa.

Once the stress interval 50 has been completed, the test subject again answers a questionnaire at a step 54, which in the current preferred embodiment would be the same questionnaire as provided to the user at steps 34 and 44.

A decision step 60 is now reached, in which it is determined whether or not more data is to be taken using this test subject. If the answer is NO, then the test has been completed, and a step 62 is reached. On the other hand, if more data is to be taken, then the YES branch is reached which directs the logic flow back to step 40, and the test subject undergoes another relaxation interval.

Figure 4:
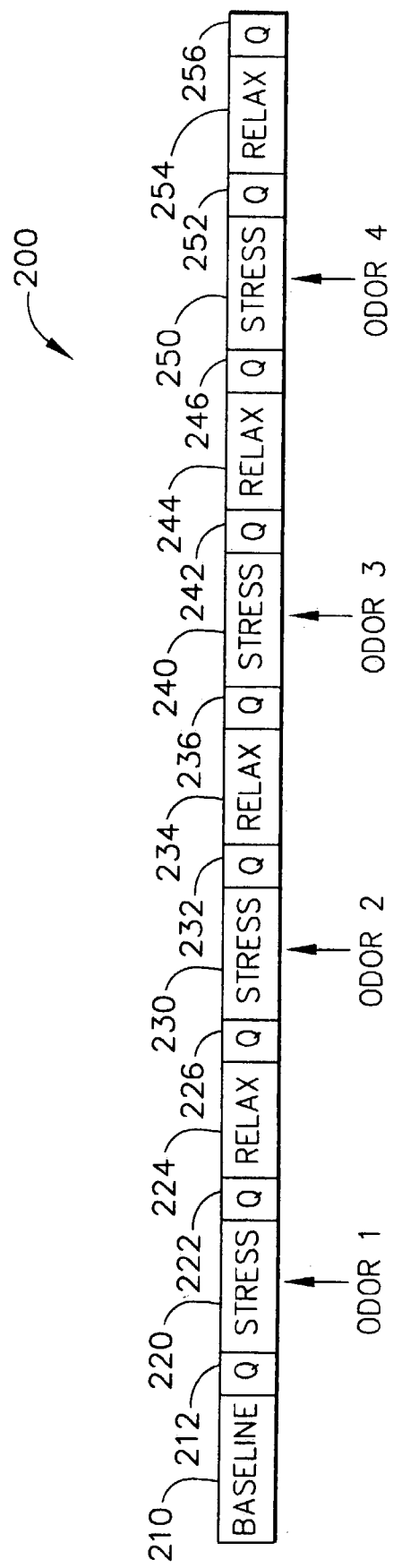
FIG. 4 is a timing diagram of a testing session using procedures depicted in the flow chart of FIG. 2, in which there are four stress-relaxation cycles.

The repetition of relaxation and stress intervals can be continued as long as is desired by the experimenter/user. FIG. 4 depicts a set of four stress-relax intervals, in which four different odors can be introduced to the test subject during the four stress intervals 220, 230, 240, and 250. Of course, in most experiments one of the stress intervals should use a blank for one of the odors, to provide the test subject's "normal" amount of acute stress as certain baseline-type data. If many test subjects are desired for testing with only a single fragrance, for example, then a minimum of two stress intervals could be used that sandwich a single relaxation interval, as depicted on the flow chart of FIG. 2.

FIG. 3 shows a hardware block diagram of a typical test setup or configuration used in the present invention. A personal computer or workstation is provided, generally designated by the reference numeral 100, and will preferably contain certain relatively standard components. Such components include a microprocessor 110, Read Only Memory (ROM) 112, Random Access Memory (RAM) 114, and some type of bulk memory storage device such as a disk drive or optical read/write memory at 116. These components are typically connected over a bus 120, through which address lines, data lines, control lines, and/or interrupt lines are run.

In the PC 100, a set of input/output drivers 130 (an interface circuit) is provided so that the PC can communicate with external hardware devices. A set of serial ports can be used to communicate with input sensors or to communicate with an output device. In general terms, the input sensors desired for the present invention include a peripheral blood flow sensor 150 and an EKG sensor 152, which communicate, respectively, through a first serial port 132 and a second serial port 134. The "EKG" sensor 152 would typically comprise multiple EKG sensor pads.

With respect to output devices, an olfactometer 160 can be used to output fragrances, and would communicate to the PC via a third serial port 136. Another output device could be a printer 140 which communicates with the PC via a parallel port 138.

In an exemplary hardware configuration, the serial ports 132 and 134 are combined into a single module that communicates with the peripheral blood flow sensor 150 and with EKG sensor 152. This will be described in greater detail below, in reference to an instrument package called Pro-Comp+™.

The olfactometer 160 will use a controller 162 that determines which fragrance, if any, is to be output into the environment within which the test subject is present. In an exemplary configuration, an air pump 164 is controlled by controller 162, as are several solenoids, such as solenoids 180, 182, and 184. When the air pump 164 is actuated, and one of the solenoids allows air to pass therethrough, then air will pass through a tube into a small chamber that contains a fragrance, thereby mixing air with a liquid fragrance and outputting that mixture into the testing environment. On FIG. 3, the first fragrance chamber is depicted at a reference numeral 170, and the air pump would drive air through the open solenoid 180 to provide an air/fragrance mixture at "Output #1." Similarly, a second fragrance chamber at 172 can be output when the air pump drives air through the open solenoid 182 until reaching an "Output #2." The number of fragrances can be as large as desired, simply by adding more fragrance chambers and more solenoids and control lines. On FIG. 3, the final fragrance chamber is enumerated at reference numeral 174, and outputs an air/fragrance mixture at "Output #N," by passing through a solenoid 184. In the illustrated depiction of FIG. 3, the chamber 174 contains water, and therefore Output #N would be the "blank" output containing no actual fragrance.

It will be understood that the order of various fragrances and the blank is entirely selectable by the experimenter/user, and the number of stress-relaxation intervals is also strictly determined by the experimenter/user. As noted above, FIG. 4 illustrates a chart 200 of a timeline that shows four sets of stress-relaxation intervals, as discussed below. Before and after each stress or relaxation interval, a questionnaire is used to provide input data that will be used to assess the test subject's psychological state with regard to stress. The first questionnaire cycle at 212 can be used to test the test subject's level of chronic stress; however, all of the other questionnaire cycles starting at 222 will preferably be used to test the subject's acute stress state. The questionnaires are described in greater detail below. As discussed above, it will be again understood that the term "fragrance" as used in this description of the present invention can represent a true fragrance or odor, or could represent a flavor (e.g., in a beverage, such as coffee, tea, soft drinks, and juices), or some type of product that includes a fragrance or flavor. In addition, the term "product" could represent some type of therapeutic or medical device, such as a THERMACARE® Neck to Arm™ wrap (with or without aroma), or perhaps a complex formulation such as a mixture of perfumes.

A product could also represent beauty and hair care products such as soaps, shower gels, shampoo, conditioners, personal cleansing; fine fragrances or colognes; home care products, such as dishwashing products, air fresheners, softeners, tissues, and towels; baby care products, such as diapers, and wipes; feminine care products, such as PMS products, or products for menopause. Other products could also include over the counter items, such as toothpaste, VAPO-RUB®, and cough syrups.

Moreover, the principles of the present invention can also be used to test the level of stress in a human test subject while performing a particular task, such as taking a shower, cleaning activities, or perhaps washing dishes or ironing clothing. While these physical tasks may, in and of themselves, be relaxing or stressful, with the present invention it is nevertheless possible to also determine if a fragrance (or "stimulus") adds or subtracts any further component of relaxation to a person's acute stress state. However, the principles of the present invention can also be used to test a person's state of stress for merely the task itself.

One advantage of the present invention is that both psychological and physiological measurements are simultaneously taken and assessed, which provides a much more accurate measure of a person's acute stress level by taking into account both body and mind (body/mind) interactions. This can be used for many purposes, but at least provides certain scientific quantifications of the psychological and physiological parameters, which have not been available in the past testing or relaxation-determinative procedures. And another important aspect of the present invention is that the physiological and psychological factors are taken in a non-invasive manner, which is a huge advantage as compared to taking blood samples or urine samples, for example, or even saliva samples.

In the present invention, the use of the questionnaire and the use of certain sensors allows the system 100 to assess the psychological and physiological effects of acute stress of a test subject (a person). The psychological questionnaires used in the SMP measure aspects of the test subject's baseline stress state and their perception of the acute stressors applied during the protocol. For physiological measurements, the neural stage of the stress response has been concentrated on, because its effects are relatively easy to measure in non-invasive ways that do not involve the hazards of dealing with bodily fluids or the expense of biochemical tests. After several exploratory panels, it has been determined that heart rate, peripheral blood flow, and pulse transit time (an inverse correlate of blood pressure) provide enough information to gauge most test subjects' physiological stress response.

In general, four physiological measures are used for quantifying stress in the present invention: heart period, pulse transit time, peripheral blood flow, and standard deviation of normal to normal beats (SDNN). These four measures typically are superior to many other parameters in measuring the physiological component of acute stress. It should be noted, however, that other non-invasive measurements could be used in addition to, or in lieu of, one or more of the above parameters. For example, muscle relaxation, skin temperature, and skin conductivity measurements can be taken with non-invasive sensors. For women undergoing PMS, muscle relaxation measurements can be an important factor in measuring physiological components of stress.

With regard to the above-noted four physiological measures, the "heart period" is the length of time between heartbeats, which is the inverse of the heart rate. An increase in heart period generally means a reduction in stress.

The "pulse transit time" is the amount of time it takes for a bolus of blood squeezed from the heart to reach the fingertip; it is an inverse analog of blood pressure. An increase in pulse transit time generally means a reduction in stress.

The "peripheral blood flow" is a measure of how much blood is flowing in capillaries near the surface of the skin. When a person is under stress, the sympathetic nervous system constricts the capillaries in the skin to shunt blood to the muscles in preparation for fight or flight. An increase in peripheral blood flow generally means a reduction in stress.

The SDNN is a measurement of heart rate variability, and is the standard deviation of the period of time between two normal heartbeats. Most persons believe that the human heart beats at a steady pace (under constant workload); however, the time between beats for a healthy heart will vary quite a bit (in the range of milliseconds for the variations). When under stress, the variation decreases; thus an increase in SDNN generally means a reduction in stress.

The SMP (the testing procedure) is a single-blinded, four-way crossover experiment designed to look for fragrance modulated differences in stress levels. In one mode of the SMP, there are four stress/relaxation cycles, as indicated in chart form at 200 on FIG. 4. A baseline interval 210 starts the testing procedure 200, followed by a questionnaire interval 212. After that has occurred, the "true" testing begins in a series of stress/relaxation cycles. It will be understood that the baseline interval 210 is not completely necessary, but it does allow the test subject to become somewhat acclimated to the testing environment.

During each four minute stress cycle (at 220, 230, 240, and 250) the test subject is exposed to a different fragrance and performs three tasks, as follows:

(1) Two minutes of oral arithmetic. The subject is given a three digit number (such as "152") and has to add up all of the digits (1+5+2=8), add the sum back to the original number (152+8=160), and report the answer orally. This is repeated with the new number ("160"), and so on, until the two minutes are up.

(2) A reaction time drill. The subject has to press the space bar on a computer as soon as they see a black square which will appear on the computer's screen after a random interval of time. This is repeated ten times.

(3) An attention task. The subject tries to keep a computer's mouse cursor centered over a small red square that moves randomly about the computer screen for 90 seconds. A score is computed for the fraction of time the cursor is over the square. (Note that this task was designed by Professor Gerd Kobal of the University of Erlangen, Germany.)

During the five minute relaxation intervals (at 224, 234, 244, and 254), the room lights are dimmed and the subject is instructed to relax in whatever way works best for them. The subject's electrocardiogram and peripheral blood flow are recorded for the duration of the experiment (i.e., the SMP procedure) to provide physiological stress data, using a computer system, such as described above in reference to FIG. 3.

To provide psychological data, each subject fills out a chronic stress questionnaire before the experiment begins (at 212) and completes an acute stress state self-report (another questionnaire) after each of the baseline, stress, and relaxation phases (i.e., at the intervals 222, 226, 232, 236, 242, 246, 252, and 256).

In an alternative embodiment, two computers may be used in the experiment. One computer can be a standard PC (such as a desktop or laptop personal computer), referred to as the "panelist computer" (not shown), which is placed within easy reach of the panelist and is used to run a computer program (called SMPadmin by the inventors) that administers all the questionnaires, self-reports, and stress tasks at the appropriate times. In this hardware configuration, a second computer is used to record the physiological data and is referred to as the "physiology computer" (see 100 on FIG. 3). A computer program (called BioGraph by Thought Technologies Ltd.), which is supplied with the ProComp+ instrument, is run on the physiology computer 100. The ProComp+ instrument package is described below in greater detail.

However, in the exemplary embodiment described in this patent document, a single computer platform is used in the experiment to acquire and record both the physiological data and the psychological data. This single computer would thereby operate as both the above-named "panelist computer" and "physiology computer," and is represented in the drawings by the reference numeral 100. Of course, the test subject (or "panelist") must be placed within easy reach of the computer 100, which is used to run the SMPadmin computer program that administers all the questionnaires, self-reports, and stress tasks at the appropriate times.

SMP Timeline:

A more detailed description of the timeline for an exemplary SMP test procedure follows in Table #1, immediately below:

TABLE #1

| Time (min) | Action |
|---|---|
| Questionnaires | Explain the experimental protocol and have panelist sign the consent form if they have not done so already. Start the SMPadmin computer program on the laptop and have the panelist fill out the chronic stress questionnaire. |
| Sensors | Start the Biograph program on the physiology computer, load the SMP screen, and begin recording so that you can see the live sensor data. Attach sensors to panelist and ensure proper placement. When you are satisfied with the sensor placement, stop recording (do not save the data) and exit Biograph. |
| 0:00 | Restart the Biograph program and load the Aroma Stress Measurement protocol. Begin recording. Take baseline measurements. Dim the lights and ask panelist to relax for 5 minutes using whatever technique works best for them. |
| 5:00 | Have panelist fill out the acute stress state questionnaire. |
| 6:00 | Turn on the lights and present Arithmetic task while panelist smells fragrance #1. |
| 8:00 | Present Reaction Time/Attention test while panelist smells fragrance #1. |
| 10:00 | Have panelist fill out the acute stress state questionnaire |
| 11:00 | Dim the lights and take away fragrance. Ask panelist to relax for 5 minutes using whatever technique works best for them. |
| 16:00 | Have panelist fill out the acute stress state questionnaire |
| 17:00 | Turn on the lights and present Arithmetic task to panelist while panelist smells fragrance #2. |
| 19:00 | Present Reaction Time/Attention test while panelist smells fragrance #2. |
| 21:00 | Have panelist fill out the acute stress state questionnaire |
| 22:00 | Dim the lights and take away fragrance. Ask panelist to relax for 5 minutes using whatever technique works best for them. |
| 27:00 | Have panelist fill out the acute stress state questionnaire |
| 28:00 | Turn on the lights and present Arithmetic task to panelist while panelist smells fragrance #3. |
| 30:00 | Present Reaction Time/Attention test while panelist smells fragrance #3. |

TABLE #1-continued

| Time (min) | Action |
|---|---|
| 32:00 | Have panelist fill out the acute stress state questionnaire |
| 33:00 | Dim the lights and take away fragrance. Ask panelist to relax for 5 minutes using whatever technique works best for them. |
| 38:00 | Have panelist fill out the acute stress state questionnaire |
| 39:00 | Turn on the lights and present Arithmetic task to panelist while panelist smells fragrance #4. |
| 41:00 | Present Reaction Time/Attention test while panelist smells fragrance #4. |
| 43:00 | Have panelist fill out the acute stress state questionnaire |
| 44:00 | Dim the lights and take away fragrance. Ask panelist to relax for 5 minutes using whatever technique works best for them. |
| 49:00 | Have panelist fill out the acute stress state questionnaire |
| 50:00 | Remove electrodes and thank panelist for participating. When the Biograph protocol comes to an end, be sure to save the data and then exit BioGraph. |

The primary measurements of interest in the experiments used in the present invention are usually the physiological changes between the stress and relaxation phases. From previous experiments, it is known that change in heart period, referred to as "Δ heart period," is usually the most reliable indicator of stress/relaxation. In addition, previous experiments have also shown that the effects of most aromas on heart period is small, but can be used to break relaxing or stimulating fragrances from the control. Because this effect is so small, it may take a large number of panelists to obtain the statistical power desired. Using heart period data gathered in a previous SMP experiment, the following Table #2 of panel sizes has been calculated. All sizes are for a level of confidence, $\alpha=0.10$.

TABLE #2

| Difference in Δ Heart Period | Test Type | Minimum Power ($\beta$) | | |
|---|---|---|---|---|
| | | 0.8 | 0.9 | 0.95 |
| 0.015 | 2-tail t | 34 | 47 | 59 |
| | 1-tail t | 25 | 36 | 47 |
| 0.010 | 2-tail t | 75 | 104 | 131 |
| | 1-tail t | 55 | 80 | 104 |
| 0.005 | 2-tail t | 300 | 413 | 523 |
| | 1-tail t | 217 | 318 | 414 |

To provide some perspective on the magnitude of heart period change between the stress and relaxation states, the mean Δ heart period for the control (blank odorant) in the first SMP test was 0.055 (SE 0.005), and the difference in mean Δ heart periods between the control and Dragoco's Lavender Mont Blanc™ (a particular fragrance) was ~0.01.

Inclusion and Exclusion Criteria:

There are some inclusion and exclusion criteria that have been used in previous experiments at The Procter & Gamble Company for general testing of fragrances. Some of these criteria are listed below, along with the rationale for some of the criteria. Depending on the target consumers, these criteria may need to be adjusted.

Inclusion Criteria:

(1) The test subject should be male or female between the ages of 20–45. The lower bound of 20 is arbitrary. After age 45 there is generally a decline in olfactory ability.

(2) The test subject should have good vision (20/20 corrected vision) and be able to see computer screen from a distance of approximately one meter, since the questionnaires and stress tasks are presented via computer.

(3) The test subject must be able to pass a pre-screening to ensure they can smell fragrances.

(4) The test subject must be willing to abstain from caffeine from midnight the day prior to the test. The physiological effects of caffeine may mask relaxation or exaggerate stimulation effects of the fragrances.

(5) The test subject must be willing to not wear perfumes or colognes the day of the test (deodorant is allowed).

Exclusion Criteria:

(1) People with heart irregularities/hypertension. Irregular heartbeat or high blood pressure will interfere with the physiologic measurements being taken.

(2) People who normally have cold hands or have been diagnosed with a poor peripheral blood circulation. Poor circulation will interfere with the physiologic measurements being taken.

(3) Smokers. Smoking dramatically decreases olfactory ability and causes a number of physiological changes that will interfere with the physiologic measurements being taken. The olfactory and physiologic changes persist for weeks after smoking stops, so smokers who say they will not smoke on the day of the test should still be excluded.

(4) People who are taking medication, using a product or participating in any study that would warrant exclusion from this study. Again, this may interfere with the physiologic measurements being taken.

(5) People with a critical electronic medical devices (e.g. pacemaker, insulin pump, etc.); this is a safety requirement to ensure there is no problem with using the ProComp+ module.

(6) Asthmatics or people with sensitivity to fragrances.

Chronic Stress Questionnaire:

The chronic stress questionnaires used in SMP, shown in Tables 3 and 4 (below), were developed by Dr. George Everly to measure frustration and overload. Both questionnaires use 40-point scales, with <20 indicating low stress, 20–24 indicating moderate stress, and >24 indicating high stress. The questionnaires are administered and scored by the SMPadmin computer program. The scores are used as a diagnostic tool to assess if the chronic stress levels of the subject population recruited for a panel matches the desired population. Previous studies that have been performed indicate that frustration and overload are both positively correlated with the changes in self-reported acute stress elicited by the stress-relaxation cycle (i.e., subjects with high frustration and overload scores tend to self-report larger differences between the stress and relaxation periods).

TABLE #3

FRUSTRATION QUESTIONNAIRE

| | almost always | often | seldom | almost never |
|---|---|---|---|---|
| Do you feel stifled or held back in your personal or professional life? | 4 | 3 | 2 | 1 |
| Do you feel a need for greater accomplishment? | 4 | 3 | 2 | 1 |
| Do you feel as though your life needs guidance or direction? | 4 | 3 | 2 | 1 |
| Do you notice yourself growing impatient? | 4 | 3 | 2 | 1 |
| Do you find yourself feeling you are in a "rut"? | 4 | 3 | 2 | 1 |
| Do you feel yourself disillusioned? | 4 | 3 | 2 | 1 |
| Do you find yourself frustrated? | 4 | 3 | 2 | 1 |
| Do you find yourself disappointed? | 4 | 3 | 2 | 1 |
| Do you find yourself upset because things haven't gone according to plan? | 4 | 3 | 2 | 1 |
| Do you find yourself feeling inferior? | 4 | 3 | 2 | 1 |

TABLE #4

OVERLOAD QUESTIONNAIRE

| | almost always | often | seldom | almost never |
|---|---|---|---|---|
| Do you find yourself with insufficient time to do things you really enjoy? | 4 | 3 | 2 | 1 |
| Do you wish you had more support/assistance? | 4 | 3 | 2 | 1 |
| Do you lack sufficient time to complete your work most effectively? | 4 | 3 | 2 | 1 |
| Do you have difficulty falling asleep because you have too much on your mind? | 4 | 3 | 2 | 1 |
| Do you feel people simply expect too much from you? | 4 | 3 | 2 | 1 |
| Do you feel overwhelmed? | 4 | 3 | 2 | 1 |
| Do you find yourself becoming forgetful or indecisive because you have too much on your mind? | 4 | 3 | 2 | 1 |
| Do you consider yourself to be in a high-pressure situation? | 4 | 3 | 2 | 1 |
| Do you feel you have too much responsibility for one person? | 4 | 3 | 2 | 1 |
| Do you feel exhausted at the end of the day? | 4 | 3 | 2 | 1 |

Acute Stress Self-Report (Questionnaire):

In some previous studies, people have assessed psychological acute stress state by bluntly asking the test subject to rate their stress at the moment on a scale from zero to ten. This is often called a "visual analog score." There are two problems with such a simplistic approach: (1) single responses tend not to be reliable, and (2) subjective stress states have a variety of components, each of which should measured. The exemplary SMP of the present invention uses a self-report that combines a new set of questions developed by the present inventors and the UWIST Mood Adjective Checklist created by Dr. Gerald Matthews (a stress expert currently at the University of Cincinnati), as modified by the present inventors.

The UWIST Mood Adjective Checklist used in the present invention is shown in Table 5, below. It has four scoring dimensions: energetic arousal, tense arousal, hedonic tone, and anger/frustration. The higher the score, the stronger a dimension contributes to the test subject's overall mood. The UWIST method has four scoring dimensions:

"Energy"—represents energetic arousal; higher scores mean a test subject feels more energetic. Range is 0–32.

"Tense"—represents tense arousal; higher scores mean a test subject feels more tension and anxiety. Range is 0–32.

"Hedonic"—represents hedonic tone; higher scores mean a test subject feels more pleasure or happiness. Range is 0–32.

"Anger"—represents anger or frustration; higher scores mean a test subject feels more anger and frustration. Range is 0–20.

The acute stress state questionnaire is administered and scored by the SMPadmin computer program between each phase of the experiment. This acute stress questionnaire comprises a checklist that includes the following statements, as seen in Table #5 below:

TABLE #5

MOOD ADJECTIVE CHECKLIST
"There is a list of words which describe people's moods or feelings. Please indicate how well each word describes how you feel AT THE MOMENT. For each word, circle the answer from 1 to 4 which best describes your mood."

| | Definitely | Slightly | Slightly Not | Definitely Not |
|---|---|---|---|---|
| 1. Happy | 1 | 2 | 3 | 4 |
| 2. Dissatisfied | 1 | 2 | 3 | 4 |
| 3. Energetic | 1 | 2 | 3 | 4 |
| 4. Relaxed | 1 | 2 | 3 | 4 |
| 5. Alert | 1 | 2 | 3 | 4 |
| 6. Nervous | 1 | 2 | 3 | 4 |
| 7. Passive | 1 | 2 | 3 | 4 |
| 8. Cheerful | 1 | 2 | 3 | 4 |
| 9. Tense | 1 | 2 | 3 | 4 |
| 10. Jittery | 1 | 2 | 3 | 4 |
| 11. Sluggish | 1 | 2 | 3 | 4 |
| 12. Sorry | 1 | 2 | 3 | 4 |
| 13. Composed | 1 | 2 | 3 | 4 |
| 14. Depressed | 1 | 2 | 3 | 4 |
| 15. Restful | 1 | 2 | 3 | 4 |
| 16. Vigorous | 1 | 2 | 3 | 4 |
| 17. Anxious | 1 | 2 | 3 | 4 |
| 18. Satisfied | 1 | 2 | 3 | 4 |
| 19. Unenterprising | 1 | 2 | 3 | 4 |
| 20. Sad | 1 | 2 | 3 | 4 |
| 21. Calm | 1 | 2 | 3 | 4 |
| 22. Active | 1 | 2 | 3 | 4 |
| 23. Contented | 1 | 2 | 3 | 4 |
| 24. Tired | 1 | 2 | 3 | 4 |
| 25. Impatient | 1 | 2 | 3 | 4 |
| 26. Annoyed | 1 | 2 | 3 | 4 |
| 27. Angry | 1 | 2 | 3 | 4 |
| 28. Irritated | 1 | 2 | 3 | 4 |
| 29. Grouchy | 1 | 2 | 3 | 4 |

Scoring the Mood Adjective Checklist:

In the following formulas, "Item(X)" means the value for the answer provided to adjective "X" in the list above. For example, if a person answered "Slightly Not" for the "Sad" adjective, then Item(20)=3.

Energy=20—(Item(3)+Item(5)+Item(16)+Item(22))+Item(7)+Item(11)+Item(19)+Item(24)

Tense=20—(Item(6)+Item(9)+Item(10)+Item(17))+Item(4)+Item(13)+Item(15)+Item(21)

Hedonic=20—(Item(1)+Item(8)+Item(18)+Item(23))+Item(2)+Item(12)+Item(14)+Item(20)

Anger=25—(Item(25)+Item(26)+Item(27)+Item(28)+Item(29))

"New" Questions Related to Physical Symptoms:

In addition to the above data set, four "new" questions provided by the present inventors relate more directly to the physical symptoms people often associate with stress, as follows:

(1) "Overall, how relaxed do you feel at the moment?"
"1 (very relaxed)–10 (not at all relaxed)"
(2) "Thinking of your head, neck, and shoulder muscles, how do you currently feel?"
"1 (completely relaxed)–10 (completely tensed)"
(3) "Thinking of your thoughts or mental state, how do you currently feel?"
"1 (I can easily concentrate/focus)–10 (I can NOT easily concentrate/focus)"
(4) "Thinking of your nerves, how do you currently feel?"
"1 (calm)–10 (anxious)"

NOTE: the higher the score, the more stressed (and less relaxed) a test subject is.

The numeric results of the above acute stress questionnaire are tabulated as described above on the computer 100 (or perhaps on a second computer) being used by the test subject. The numeric results are compiled so that a "complete" report of the test subject's psychological components and physiological components can be summarized on a single computer platform. An example of such summarized reports is provided below, in connection with the description of FIGS. 10–13.

As can be seen from the above description of the questionnaire, the test subject is required to answer multiple "quick-answer" questions that are involved with mood components, or with determining perceived physiological effects of acute stress. These questions tend to provide a measure of the test subjects' psychological state.

Fragrance Administration:

The SMP experiment is designed to test three fragrances and one blank (e.g., water). The blank is usually considered essential, because it provides the baseline stress/relaxation response that the fragrances will be compared to. The fragrances should be diluted to a strength that is appropriate to the purpose of the experiment and, if possible, to similar perceived strengths. If an olfactometer is available, it can be used to administer the fragrances. Otherwise, the fragrances can be presented to the test subject by saturating equal-sized strips of filter paper with the fragrance and placing the filter paper in an open wide-mouth jar placed approximately one foot from and level with the test subject's chin. The room in which the experiment is conducted should be designed for high air turnover (at least eight complete air changes per hour is recommended) or, at a minimum, have a fume hood.

The fragrances may be presented according to the following exemplary schedule (see Table #6) in order to test for carry-over effects during statistical analysis:

TABLE #6

| Subject | Stress Phase | | | |
|---|---|---|---|---|
| | 1 | 2 | 3 | 4 |
| 1 | A | B | D | C |
| 2 | B | C | A | D |
| 3 | C | D | B | A |
| 4 | D | A | C | B |

The test ordering can be repeated for each block of four subjects. It is permissible to randomize the rows within each block of four subjects if desired. If the number of panelists in a particular panel is not a multiple of four, then it is permissible to use the schedule of Table #6 in the available groups of four, and into the final grouping that is less than four. In most situations, it is recommended that the blank be fragrance A, and would be a requirement if the statistical analysis software expects fragrance A to be the blank.

Recording the Physiological Signals:

As noted above, the physiological data is recorded using a ProComp+ biofeedback instrument, manufactured by Thought Technologies, Ltd. (www.thoughttechnology.com). The ProComp+ module is an eight-channel digital system (i.e., an interface circuit) able to monitor EMG, EEG, temperature, heart rate, blood volume pulse, skin conductance, EKG, and respiration. The user can monitor one, all, or mix-and-match channels. In the SMP experiment, only two channels are used: the EKG and blood volume pulse sensors. The ProComp+ module connects to a serial port on the physiology computer 100 using a fiber optic cable, eliminating the possibility of electrical shock from the computer.

The BioGraph computer program is used to view and record the signals from the ProComp+ module. The BioGraph User's Manual provides instructions on how to install, configure, and use the ProComp+ module. For example, to view the signals during sensor placement, start BioGraph, click the "Load a Screen" button, double-click on the "SMP" screen, and then click on the record button. The signals will be displayed in the two graphs on the screen. It is important that the sensors are adjusted (i.e., their positions) until "good" signals are received, or else the stress measurement software will not perform well. When the user is satisfied with the sensor placement, the user may stop recording (the data need not be saved) and exit the BioGraph program. To record the data during an experiment, restart BioGraph and load the "Aroma Stress Measurement" protocol (the computer program created by the present inventors). This protocol will guide the user through the various phases of the experiment.

Figure 5:
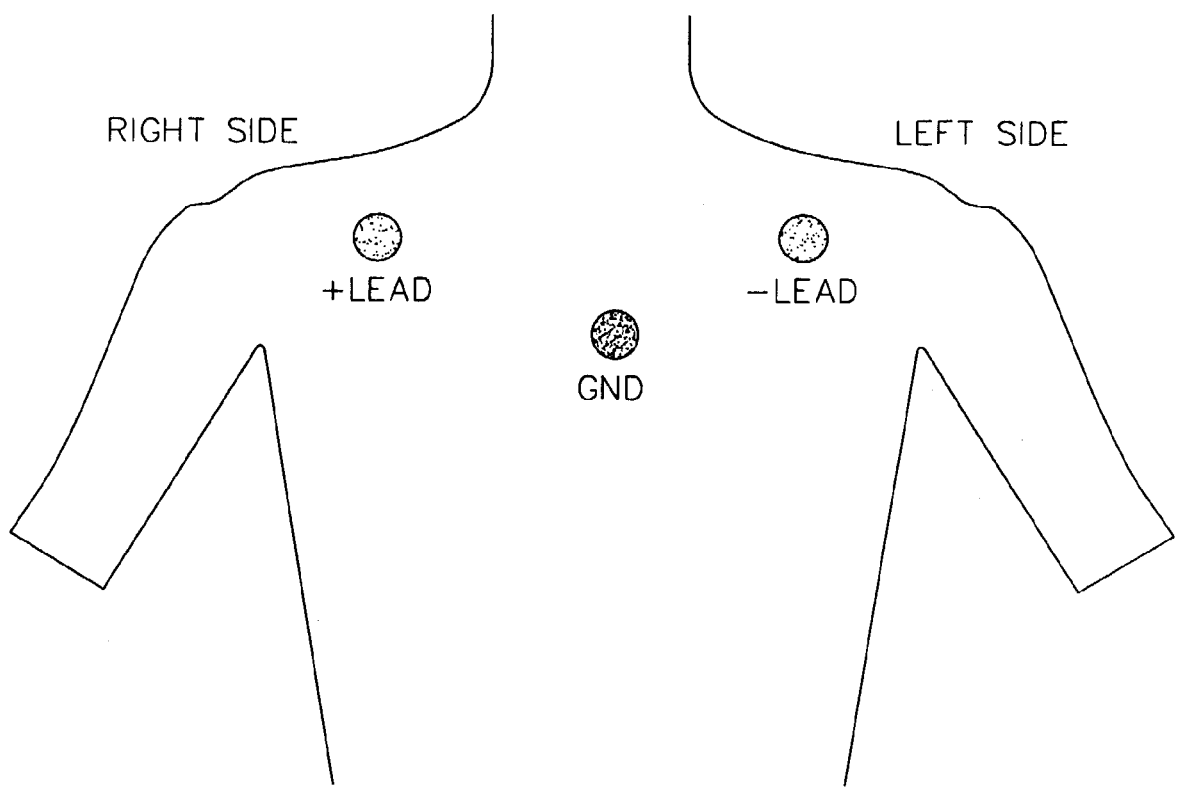
FIG. 5 is a diagrammatic view of attachment locations of EKG electrodes used in the testing procedure of FIG. 2.
Figure 6:
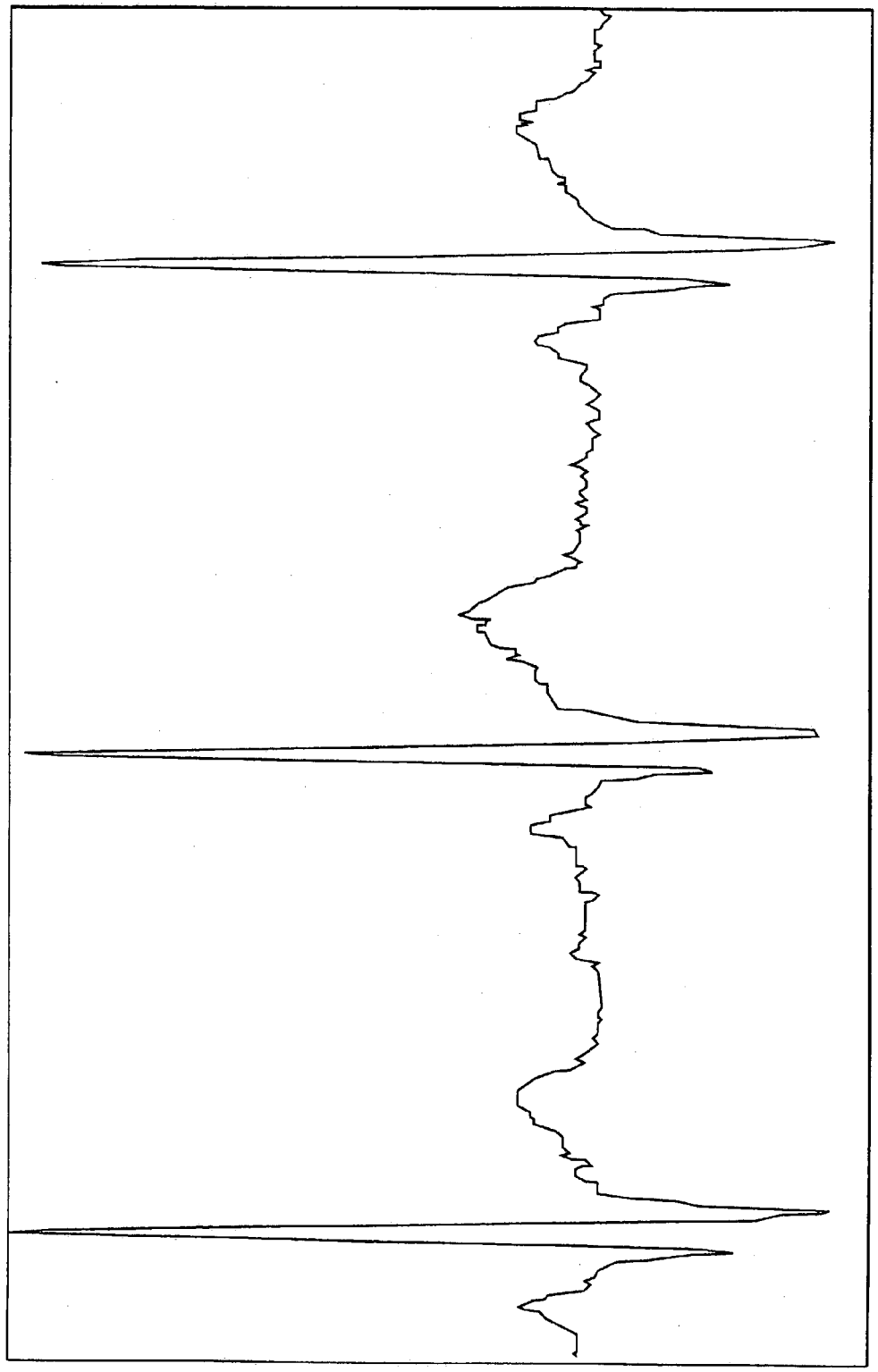
FIG. 6 is a graph showing a sample EKG signal.

EKG Sensor:

The EKG sensor (152 on FIG. 3) should be plugged into Channel A of the ProComp+ module (e.g., serial port 132), with the extension leads attached. Disposable silver/silver chloride EKG electrodes embedded in an adhesive foam strip are used to attach the sensor leads to the test subject. A small amount of electrode gel should be used to improve the electrical connection with the subject. The positive (+) lead is attached to the subject's right clavicle, the negative (−) lead is attached to the left clavicle, and the ground (black) lead is attached to the sternum (see FIG. 5). The exact attachment site is not critical, as long as a strong QRS spike is recorded for each heartbeat. See FIG. 6 for an exemplary shape of the QRS spike of an EKG waveform.

Figure 7:
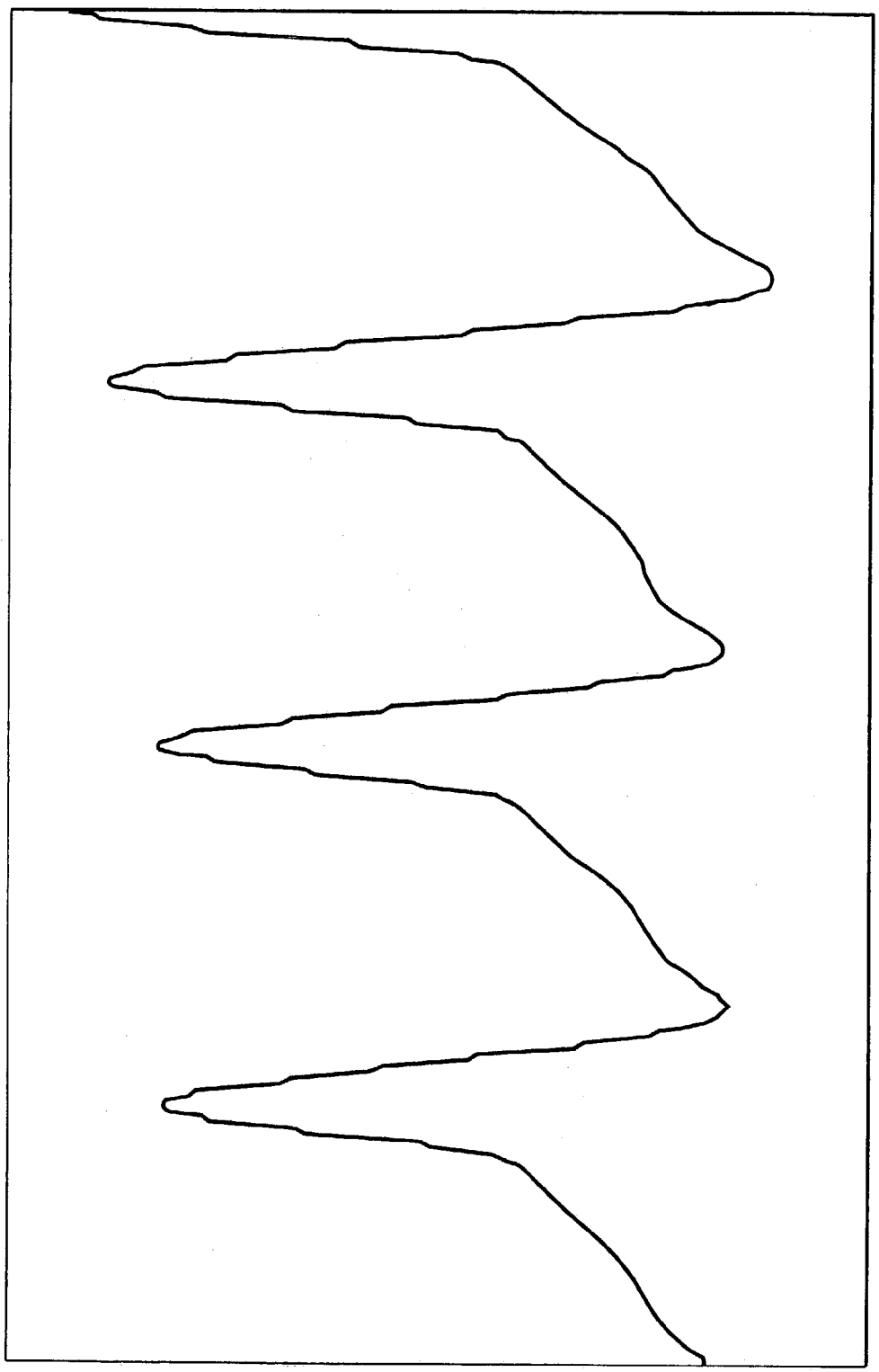
FIG. 7 is a graph showing a sample BVP signal.

Peripheral blood flow is detected using a blood volume pulse (BVP) sensor 150, which is a photoplethysmograph. The BVP sensor 150 should be plugged into Channel B of the ProComp+ module (e.g., serial port 134). It should be noted that the BioGraph manual uses Channel H for the BVP, which is sampled at 32 Hz. However, for the SMP experiment, Channel B is recommended, which has a higher sampling rate of 256 Hz. The BVP sensor 150 should taped to the tip of the middle finger of the test subject's non-dominant hand, and care should be taken to not tape it too tightly, or the subject's finger may start to throb during the experiment. A typical peripheral blood flow signal (the BVP signal) is illustrated in FIG. 7.

Preparing the Data for Analysis:

The recorded signals are used to calculate the average heart period, average pulse transit time, and average peripheral blood flow of each test subject for each phase of the experiment. To compute these values, the location of the heartbeats within each signal must be determined. It is also important to identify any portions of the signals that are corrupted by artifacts and, therefore, which should be ignored. All of these tasks are performed using a computer program named "HeartEd," written by one of the present inventors.

There is a separate user's manual for the HeartEd computer program that describes how to edit the heartbeat data. Some of the more significant steps in the data preparation process are discussed, immediately below:

(1) After all of the panelist data has been completed, the raw data should be archived to CD-ROM or some other storage media. The signal data is found in the "C:\BIOGRAPH\DATA" directory of the physiology computer 100 and the questionnaire, reaction time, and attention test data is located in the "C:\PROGRAM FILES\SMPadmin" directory of the computer 100 (or, if two computer platforms are used, the "C:\PROGRAM FILES\SMPadmin" directory is resident on the panelist computer (not shown)).

(2) The "File|Migrate BioGraph Files" command in the HeartEd program is used to copy the signal data to a working directory where all of the analysis files will be stored.

(3) The "*.dat" files should be copied from the "C:\PROGRAM FILES\SMPadmin" directory of the panelist computer to the working directory specified in step (2), above.

(4) Execute the "File|Create New Study using Template" command in the HeartEd program and open the "SMP.tpl" template file. In the Study Properties dialog, set the directory of the new study file to be the working directory that was specified as the migration target in step (2), above.

(5) Edit the heartbeat locations as necessary for every segment of each subject in the study.

(6) Execute the "File|Generate Measurements File" command in the HeartEd program.

(7) After the procedure has been completed, the working directory should be archived.

(8) Before running the procedure on another panel, be sure to delete all the subdirectories in the "C:\BIOGRAPH\DATA" directory and the "*.dat" files from the "C:\PROGRAM FILES\SMPadmin" directory of the panelist computer.

Statistical Analysis:

The statistical analysis of the panel data is performed by a computer program called ASMPstat by the present inventors, which invokes an analysis routine provided by a computer program called SAS® (sold by SAS Institute, Inc. located in Cary, N.C.) to test if any of the psychological or physiological measurements associated with a fragrance are different than those associated with the blank. The SAS statistical analysis routine incorporates terms for period, product, sequence, and subject (nested within sequence). The statistical model used in ASMPstat is tied to the design of the experimental procedure of the present invention.

Figure 8:
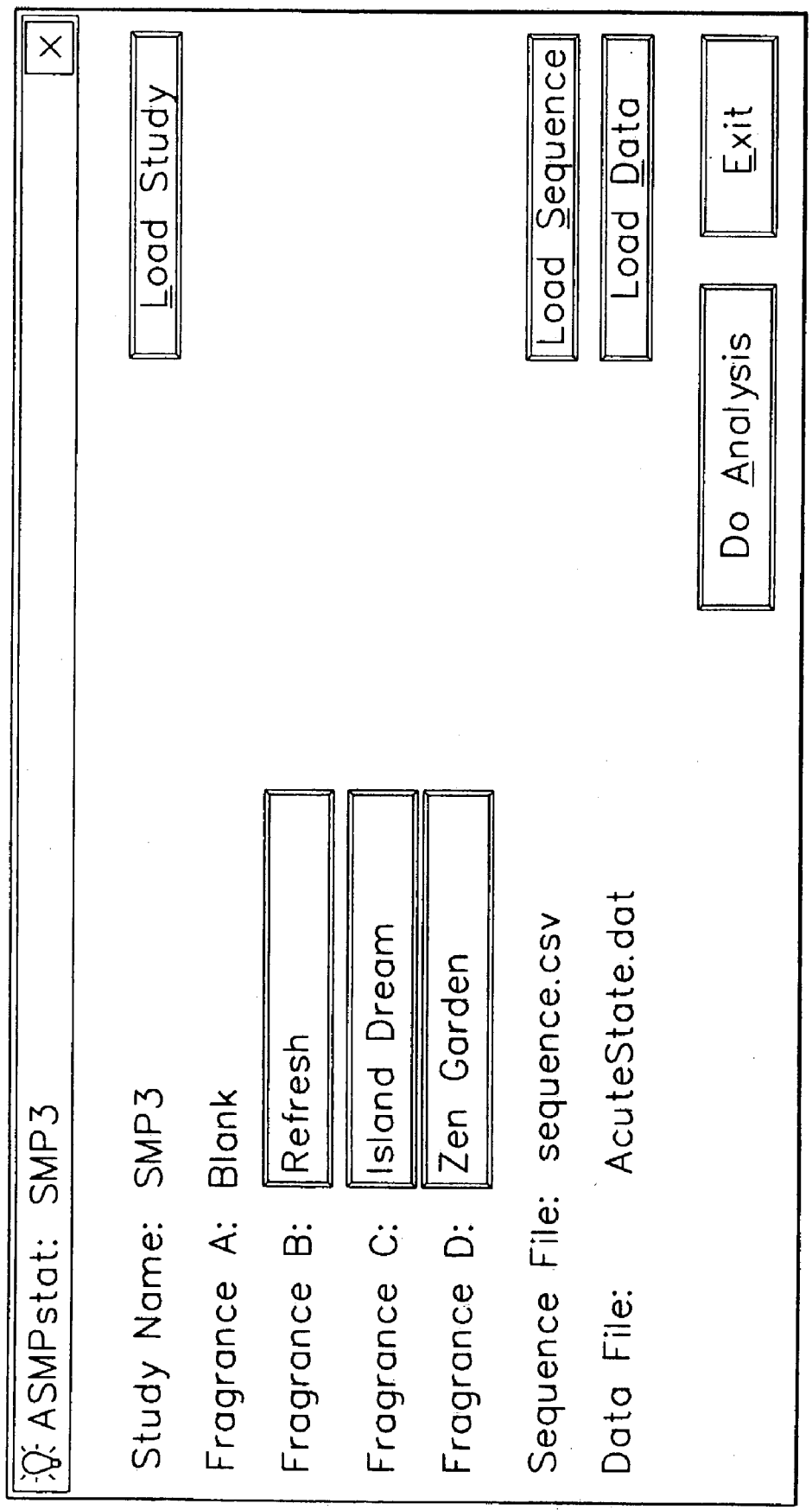
FIG. 8 is a diagrammatic view of one of the displays used in an ASMPstat computer program, used in the testing procedure of FIG. 4.

A screen shot of the ASMPstat computer program is shown in FIG. 8. The following steps are recommended for use of this program, as follows:

(1) Create a comma separated value (.csv) file that contains two columns of data, with headings of "Subject" and "Sequence". The "Subject" column contains the ID used for each test subject in the panel and the "Sequence" column contains the odor presentation sequence for each panelist. The sequence should use the numbers 1–4 instead of the letters A–D. (A ".csv" file can be created from Excel by using the "File|Save As" command and selecting csv as the file type.)

(2) Click the "Load Study" button and select the study file that was created with the HeartEd computer program.

(3) Type in the names of the fragrances used in the test.

(4) Click the "Load Sequence" button and select the sequence file that was created in step (1), above.

(5) Click the "Load Data" button and select either the psychological data in the study's "AcuteState.dat" file or the physiological data in the study's "HeartMeasures.dat" file.

(6) Click on the "Do Analysis" button to launch SAS and perform the statistical analysis. The results of the analysis are in the text files "Report.txt," which contains the analysis highlights, and "Report.1st", which is the detailed SAS output which should be consulted in the event of any errors or problems with the analysis.

The ASMPstat computer program only processes one data file at a time and it presently is designed to write its output to the files "Report.txt" and "Report.1st", so the program must be run twice in order to process the psychological and the physiological data. The report output files should be renamed before running ASMPstat a second time!

The "Report.txt" file contains two tables that are best viewed in Microsoft Word®. The first table, titled "Overall Means for Average Change," indicates if there is evidence that any of the measurements listed in the rows of the table were different during the stress and relaxation phases, without regard to the fragrances. In statistical terms, the null hypothesis for these tests is that there is no difference in the measurements taken during the four stress phases versus the measurements taken during the four relaxation phases.

The key values in the Overall Means for Average Change table are in the column headed "Prob>|T|". If the value in this column is greater than the level of confidence, $\alpha$, then the measurement in that row could not statistically break the stressed phases versus the relaxed phases and, therefore, any results in the second table for that measurement should be ignored. An example of this table is shown in Table #7, below (note: "SMP3" is the name of the study):

TABLE #7

SMP3
OVERALL MEANS FOR AVERAGE CHANGE
41 SUBJECTS

| Variable | # of Values | Mean | Std Dev | Std Error | T | Prob > |T| |
|---|---|---|---|---|---|---|
| Relax | 164 | 1.427 | 1.654 | 0.129 | 11.045 | <0.0001 |
| Muscle | 164 | 1.012 | 1.482 | 0.116 | 8.747 | <0.0001 |
| Focus | 164 | 0.262 | 1.840 | 0.144 | 1.825 | 0.0698 |
| Nerves | 164 | 1.122 | 1.597 | 0.125 | 8.999 | <0.0001 |
| Scent_Likability | 164 | 0.000 | 0.000 | 0.000 | . | <0.0001 |
| Scent_Strength | 164 | 0.000 | 0.000 | 0.000 | . | <0.0001 |
| Energetic | 164 | 2.207 | 3.621 | 0.283 | 7.807 | <0.0001 |
| Tense | 164 | 3.470 | 4.117 | 0.321 | 10.792 | <0.0001 |
| Hedonic | 164 | −1.244 | 2.162 | 0.169 | −7.366 | <0.0001 |
| Anger | 164 | 0.756 | 1.847 | 0.144 | 5.242 | <0.0001 |

If the level of confidence is 0.10, then all of the measurements in the table are able to statistically break stressed versus relaxed. However, if the level of confidence is 0.05, then the "Focus" measurement is not valid for this experiment, so all of the focus measurements in the second table should be ignored. The values in the "Scent Likability" and "Scent Strength" rows will always be zero, because the scent questions are only asked during the stress phases, and thus these rows should be ignored.

The second above-mentioned table is titled "Table of Least Squares Means(SE)," which contains information comparing the effects of each fragrance versus the blank. Each measurement is presented in a separate row of the table. The "Type" column indicates if the comparison is being made between the stress phase, the relaxation phase, or the change (delta) between the stress and relaxation phases. The "Treatment Pr>F" column indicates the level of evidence supporting the null hypothesis that the fragrances had no effect on the measurement. If this value is greater than the confidence level, then the row should be ignored entirely. The remaining columns list data for each fragrance. The "Pr>|T|" columns indicate the level of evidence supporting the null hypothesis that the effect of a particular fragrance is no different than that of the blank. If the value in this column is less than or equal to the confidence level, then there is evidence that the fragrance had an effect. The fragrance's mean should be compared to the blank's mean to determine if the effect was relaxing or stimulating.

An example of this second table (Table of Least Squares Means(SE)) is provided below in Table #8, below:

that of the blank, meaning that subjects found it easier to concentrate/focus while they were exposed to Fragrance B. In the "Energetic" stress phase row, both Fragrances B and C are significantly different from the blank. Both fragrances' averages are higher than the blank's, which means that subjects felt like they had more energy while exposed to Fragrances B and C.

By using both a peripheral blood flow sensor and the EKG monitor, it is possible to determine the pulse transit time of the heartbeat between the heart and the finger to which the peripheral blood flow sensor is attached. The higher the person's blood pressure, the faster the transit time. On the other hand, if only a single sensor is used to input physiological data, then the pulse transit time could not be determined. However, other important data can still be received by a single sensor: (1) if the EKG sensor alone is used, then the person's heart rate and heart rate variability can be determined; (2) if the peripheral blood flow (PBF) sensor alone is used, then the heart rate and heart rate variability can be determined, as well as the peripheral blood flow.

Figure 9:
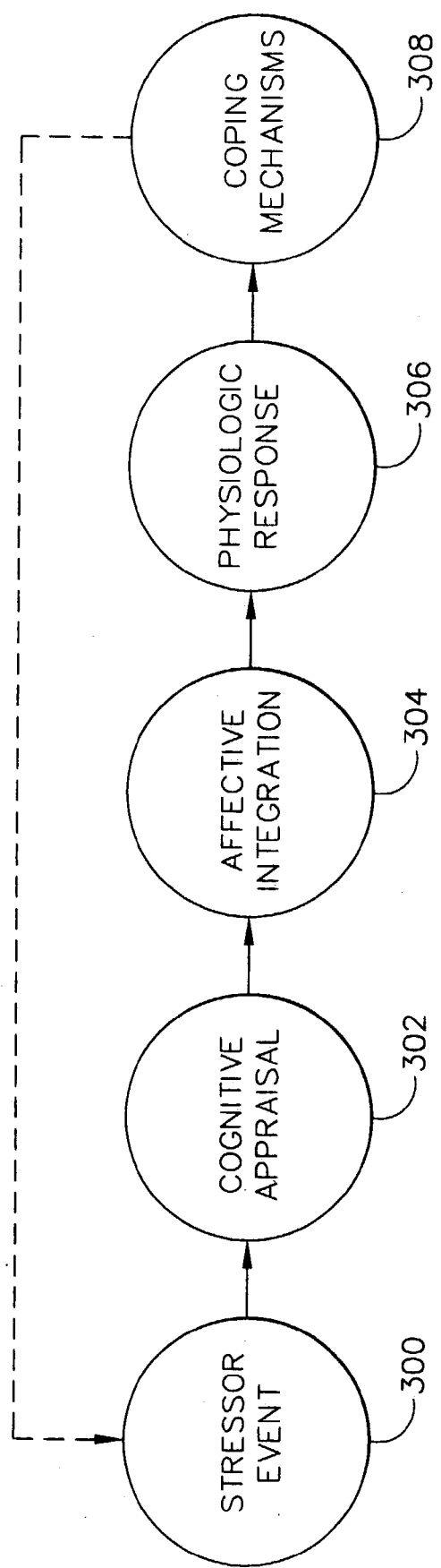
FIG. 9 is a second diagram of a model of the human stress response, known in the prior art.
Figure 10:
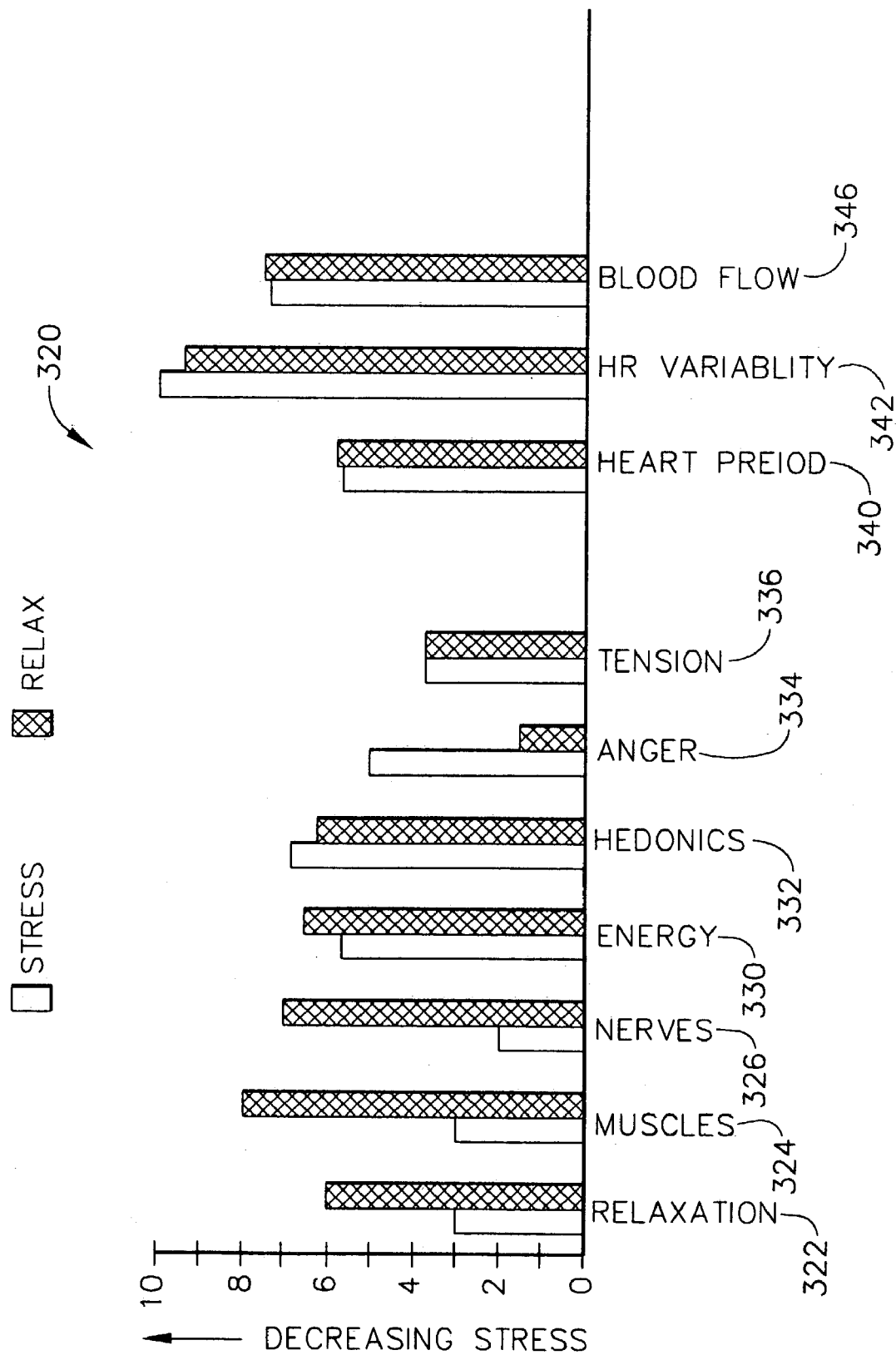
FIG. 10 is a bar chart of an example stress profile of a test subject, as according to the testing procedure of FIG. 4.

FIG. 9 depicts another human stress response model, this time describing the various stages in a somewhat different

TABLE #8

SMP3
Table of Least Squares Means(SE) - 41 Subjects

| Variable | Type | # of Values | Treatment Pr > F | Blank Mean(SE) | Fragrance A Mean(SE) | Pr > |T| | Fragrance B Mean(SE) | Pr > |T| | Fragrance C Mean(SE) | Pr > |T| |
|---|---|---|---|---|---|---|---|---|---|---|
| Relax | Stress | 164 | 0.9314 | 4.302 (0.206) | 4.339 (0.206) | 0.8992 | 4.349 (0.206) | 0.8718 | 4.177 (0.206) | 0.6695 |
| Relax | Relax | 164 | 0.9248 | 2.924 (0.119) | 2.850 (0.119) | 0.6623 | 2.823 (0.119) | 0.5518 | 2.824 (0.119) | 0.5565 |
| Relax | Delta | 164 | 0.9023 | 1.378 (0.192) | 1.489 (0.192) | 0.6837 | 1.526 (0.192) | 0.5871 | 1.353 (0.192) | 0.9267 |
| Muscle | Stress | 164 | 0.8341 | 4.828 (0.170) | 4.725 (0.170) | 0.6692 | 4.701 (0.170) | 0.5973 | 4.606 (0.170) | 0.3577 |
| Muscle | Relax | 164 | 0.8758 | 3.743 (0.110) | 3.693 (0.110) | 0.7503 | 3.716 (0.110) | 0.8660 | 3.621 (0.110) | 0.4324 |
| Muscle | Delta | 164 | 0.9706 | 1.086 (0.169) | 1.032 (0.169) | 0.8230 | 0.985 (0.169) | 0.6727 | 0.986 (0.169) | 0.6763 |
| Focus | Stress | 164 | 0.0395 | 4.471 (0.213) | 4.433 (0.213) | 0.9011 | 3.691 (0.213) | 0.0108 | 4.131 (0.213) | 0.2614 |
| Focus | Relax | 164 | 0.0302 | 4.147 (0.163) | 4.109 (0.163) | 0.8689 | 3.525 (0.163) | 0.0079 | 3.884 (0.163) | 0.2555 |
| Focus | Delta | 164 | 0.9633 | 0.323 (0.246) | 0.324 (0.246) | 0.9986 | 0.166 (0.246) | 0.6517 | 0.246 (0.246) | 0.8254 |
| Nerves | Stress | 164 | 0.9944 | 4.106 (0.203) | 4.077 (0.203) | 0.9175 | 4.052 (0.203) | 0.8505 | 4.126 (0.203) | 0.9455 |
| Nerves | Relax | 164 | 0.8079 | 3.021 (0.130) | 2.925 (0.130) | 0.6043 | 3.020 (0.130) | 0.9949 | 2.870 (0.130) | 0.4158 |
| Nerves | Delta | 164 | 0.8808 | 1.085 (0.204) | 1.151 (0.204) | 0.8193 | 1.032 (0.204) | 0.8546 | 1.256 (0.204) | 0.5563 |
| Scent_Likability | Stress | 164 | <0.0001 | 6.084 (0.257) | 4.437 (0.257) | <0.0001 | 4.419 (0.257) | <0.0001 | 4.583 (0.257) | <0.0001 |
| Scent_Likability | Relax | 164 | <0.0001 | 6.084 (0.257) | 4.437 (0.257) | <0.0001 | 4.419 (0.257) | <0.0001 | 4.583 (0.257) | <0.0001 |
| Scent_Likability | Delta | 164 | <0.0001 | 0.000 (.) | 0.000 (.) | <0.0001 | 0.000 (.) | <0.0001 | 0.000 (.) | <0.0001 |
| Scent_Strength | Stress | 164 | <0.0001 | 8.383 (0.250) | 6.660 (0.250) | <0.0001 | 6.717 (0.250) | <0.0001 | 7.251 (0.250) | 0.0018 |
| Scent_Strength | Relax | 164 | <0.0001 | 8.383 (0.250) | 6.660 (0.250) | <0.0001 | 6.717 (0.250) | <0.0001 | 7.251 (0.250) | 0.0018 |
| Scent_Strength | Delta | 164 | <0.0001 | 0.000 (.) | 0.000 (.) | <0.0001 | 0.000 (.) | <0.0001 | 0.000 (.) | <0.0001 |
| Energetic | Stress | 164 | 0.0900 | 21.061 (0.394) | 21.742 (0.394) | 0.2241 | 22.378 (0.394) | 0.0198 | 22.073 (0.394) | 0.0719 |
| Energetic | Relax | 164 | 0.4520 | 19.523 (0.321) | 19.375 (0.321) | 0.7444 | 20.061 (0.321) | 0.2378 | 19.529 (0.321) | 0.9906 |
| Energetic | Delta | 164 | 0.3237 | 1.538 (0.413) | 2.367 (0.413) | 0.1579 | 2.316 (0.413) | 0.1847 | 2.544 (0.413) | 0.0871 |
| Tense | Stress | 164 | 0.3187 | 16.978 (0.453) | 17.364 (0.453) | 0.5484 | 17.407 (0.453) | 0.5044 | 16.342 (0.453) | 0.3228 |
| Tense | Relax | 164 | 0.5488 | 13.626 (0.295) | 13.556 (0.295) | 0.8665 | 13.765 (0.295) | 0.7401 | 13.184 (0.295) | 0.2911 |
| Tense | Delta | 164 | 0.7236 | 3.352 (0.438) | 3.808 (0.438) | 0.4626 | 3.642 (0.438) | 0.6396 | 3.158 (0.438) | 0.7544 |
| Hedonic | Stress | 164 | 0.3242 | 25.341 (0.318) | 25.215 (0.318) | 0.7803 | 25.662 (0.318) | 0.4766 | 25.982 (0.318) | 0.1567 |
| Hedonic | Relax | 164 | 0.3320 | 26.568 (0.227) | 26.820 (0.227) | 0.4345 | 26.682 (0.227) | 0.7239 | 27.132 (0.227) | 0.0821 |
| Hedonic | Delta | 164 | 0.5764 | −1.227 (0.308) | −1.605 (0.308) | 0.3886 | −1.020 (0.308) | 0.6357 | −1.150 (0.308) | 0.8595 |
| Anger | Stress | 164 | 0.5803 | 7.409 (0.228) | 7.257 (0.228) | 0.6370 | 7.218 (0.228) | 0.5541 | 6.964 (0.228) | 0.1700 |
| Anger | Relax | 164 | 0.6865 | 6.522 (0.162) | 6.428 (0.162) | 0.6836 | 6.545 (0.162) | 0.9193 | 6.294 (0.162) | 0.3222 |
| Anger | Delta | 164 | 0.8952 | 0.887 (0.246) | 0.828 (0.246) | 0.8656 | 0.673 (0.246) | 0.5385 | 0.670 (0.246) | 0.5329 |

Figure 1:
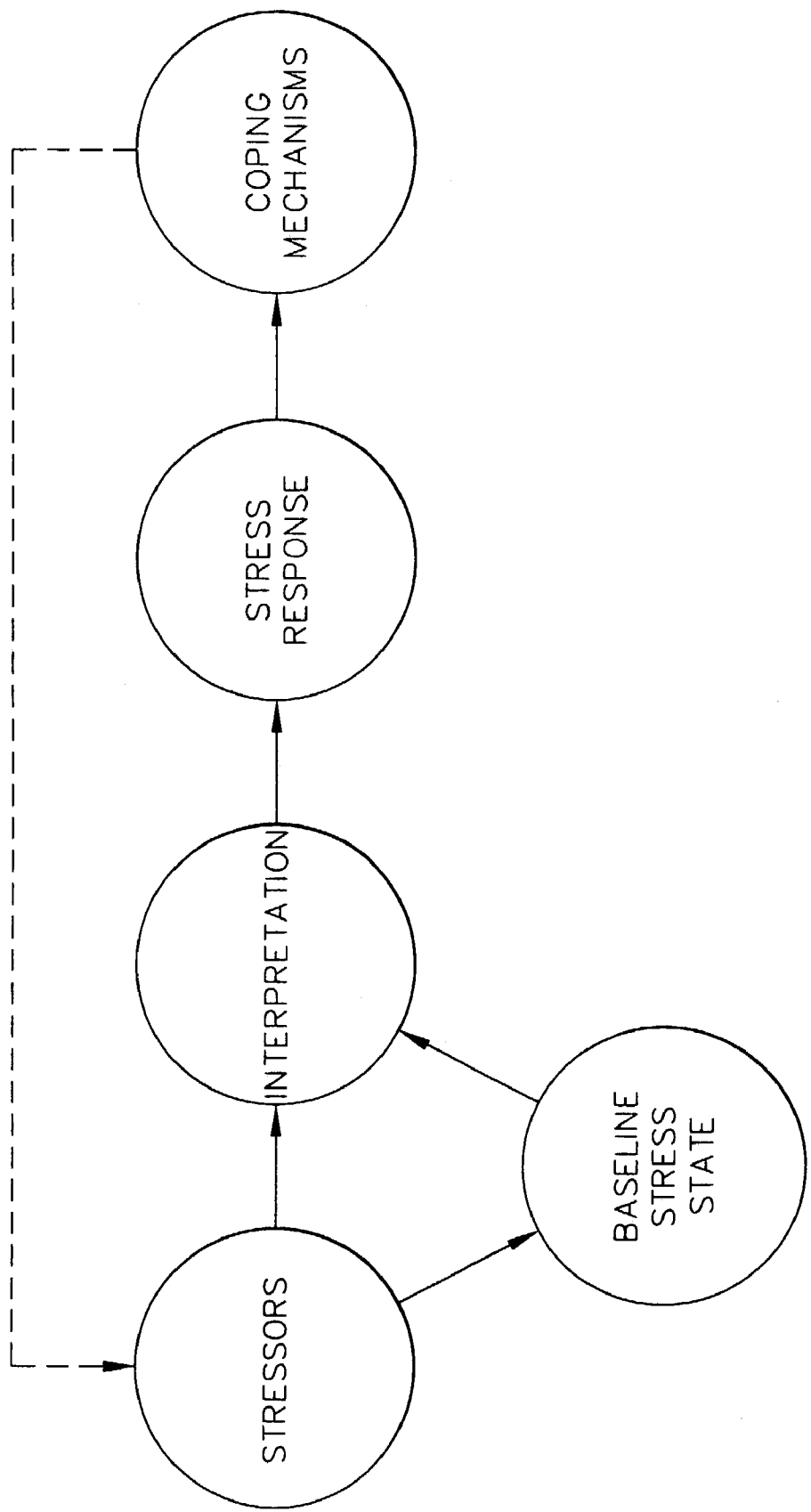
FIG. 1 is a diagram of a model of the human stress response, known in the prior art.

With a treatment confidence level of α 0.10, the "Scent Likability," "Scent Strength," "Focus" (stress and relaxation phases), and "Energetic" (stress phase only) measurements show a treatment effect; all other rows should be ignored. The scent likeability and strength data do not reflect aromatheraputic action. Using a confidence level of α=0.10, within the "Focus" rows only Fragrance B shows an effect different from the blank. In both the stress and relaxation phases the average Focus measurement for Fragrance B is lower than manner than that of FIG. 1. The stressor event is indicated at 300, after which the first thing to occur to a person is cognitive appraisal, as seen at a step 302. This cognitive appraisal stage is a psychological component of acute stress. The next stage at 304 is affective integration, which also is a psychological component of acute stress.

The next stage at 306 is the physiologic response, which is the first physiological component of acute stress. The final stage at 308 represents the coping mechanisms, which are the action that the body takes after undergoing the psychological and physiological components of the stress response model.

With respect to psychological measurements, some measurements can be determined relating to the following attributes: muscles, relaxation, nerves, and focus; a second set of attributes are: energy, hedonic, tension, and anger. Each of these components can be determined both before a stressor or relaxation event, and after the event. Furthermore, if a fragrance (or product or flavor, for example) is introduced, then a third set of data can be determined that would represent the psychological components during or after a stress event or a relaxation event as affected by the fragrance or aroma introduction.

With regard to physiological components of acute stress, the sympathetic nervous system is activated upon introduction of acute stress, and some of the physiological effects are as follows: the person's pupils dilate, the capillaries near the skin constrict, the heart rate increases, the bronchi dilate, the muscles tense, and stomach motility is inhibited. Some of these physical or physiological effects can be measured by the sensors described above, in reference to the present invention.

The questionnaires described above are used to analyze the person's (i.e., the test subject's) psychological stress profile, in a manner that can be assessed and computed by the PC/workstation 100. An example of the results is provided as bar charts in FIGS. 10 and 11. On FIG. 10, a bar chart 320 is provided that illustrates some of the psychological and physiological components of stress. The Y-axis represents stress, in which the greater the number along the positive scale, the lower the level of stress. The X-axis represents the various attributes (or components).

The first three components represent relaxation at 322, muscles at 324, and nerves at 326. These three components are physiological effects due to certain psychological components, as evaluated by the "new questions" that more relate to the physical symptoms people often associate with stress, as noted above. The chart 320 does not include the "focus" attribute, although that could be included if desired. The present inventors have determined that the "focus" attribute is less useful than the relaxation, muscles, and nerves attributes.

The next four components are related to the "mood" of the test subject, and include energy at 330, hedonics at 332, anger at 334, and tension at 336. These components are determined from the list of twenty-nine adjectives that the test subject answers at each questionnaire, as described in reference to Table #5, above. The evaluation of these twenty-nine adjective "questions" is well known in the prior art, as discussed above.

The final three components represent the physiological effects that were measured by the computer system 100 from the physical instrumentation of the peripheral blood flow sensor 150 and EKG sensor 152. These components are as follows: heart period at 340, heart rate variability at 342, and blood flow at 346.

Figure 11:
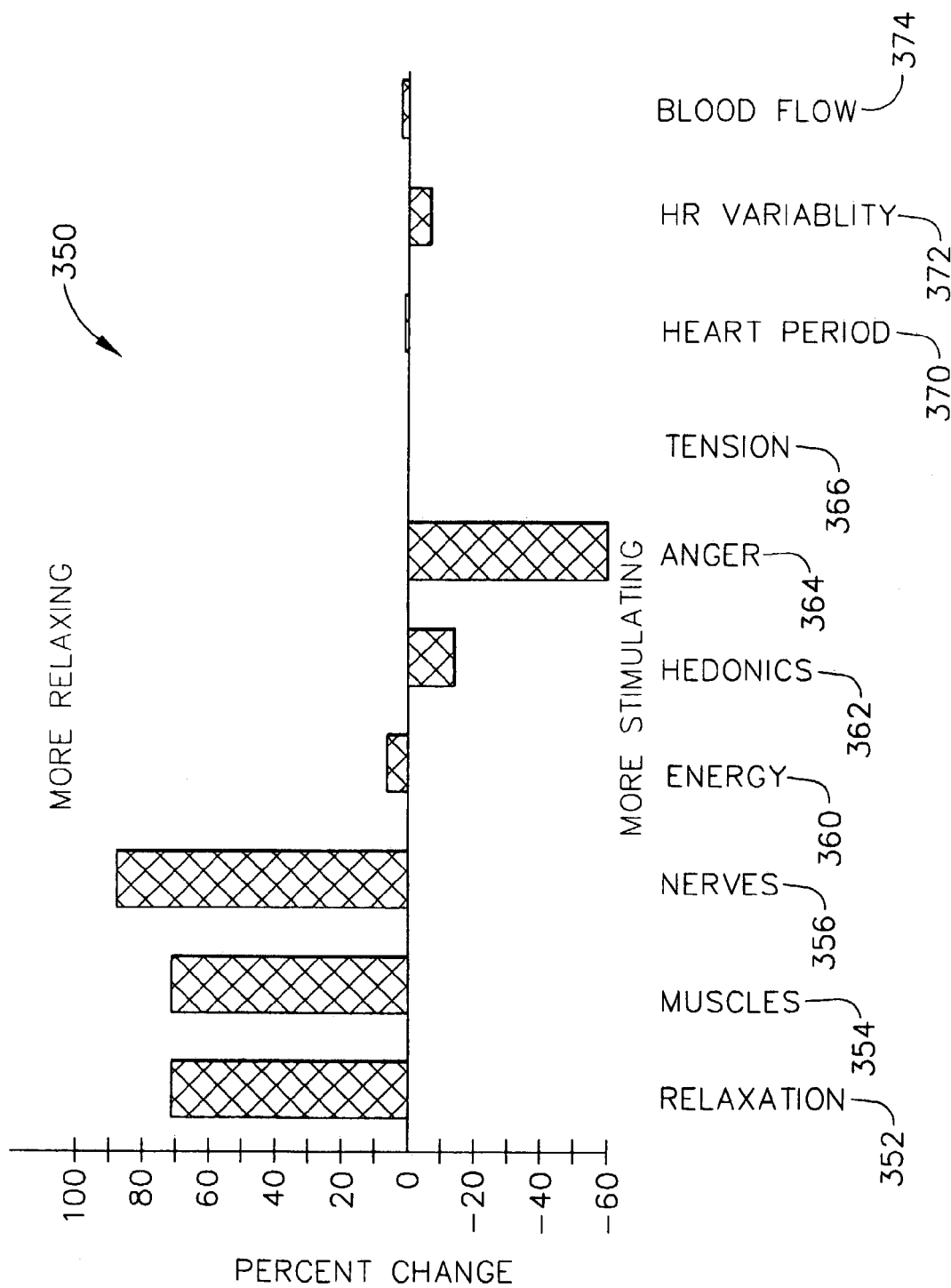
FIG. 11 is a bar chart of a test subject's stress profile of FIG. 10, showing the differential between stress and relaxation conditions.

The differential results between a stress interval and a relaxation interval can be depicted on a bar chart, such as illustrated in the graph 350 on FIG. 11. The same eleven components are listed, as follows: relaxation at 352, muscles at 354, nerves at 356, energy at 360, hedonics at 362, anger at 364, tension at 366, heart period at 370, heart rate variability at 372, and blood flow at 374. A positive percent change means that a component had a "more relaxing" effect, while a negative percent change indicates that the particular component had a "more stimulating" effect.

Figure 12:
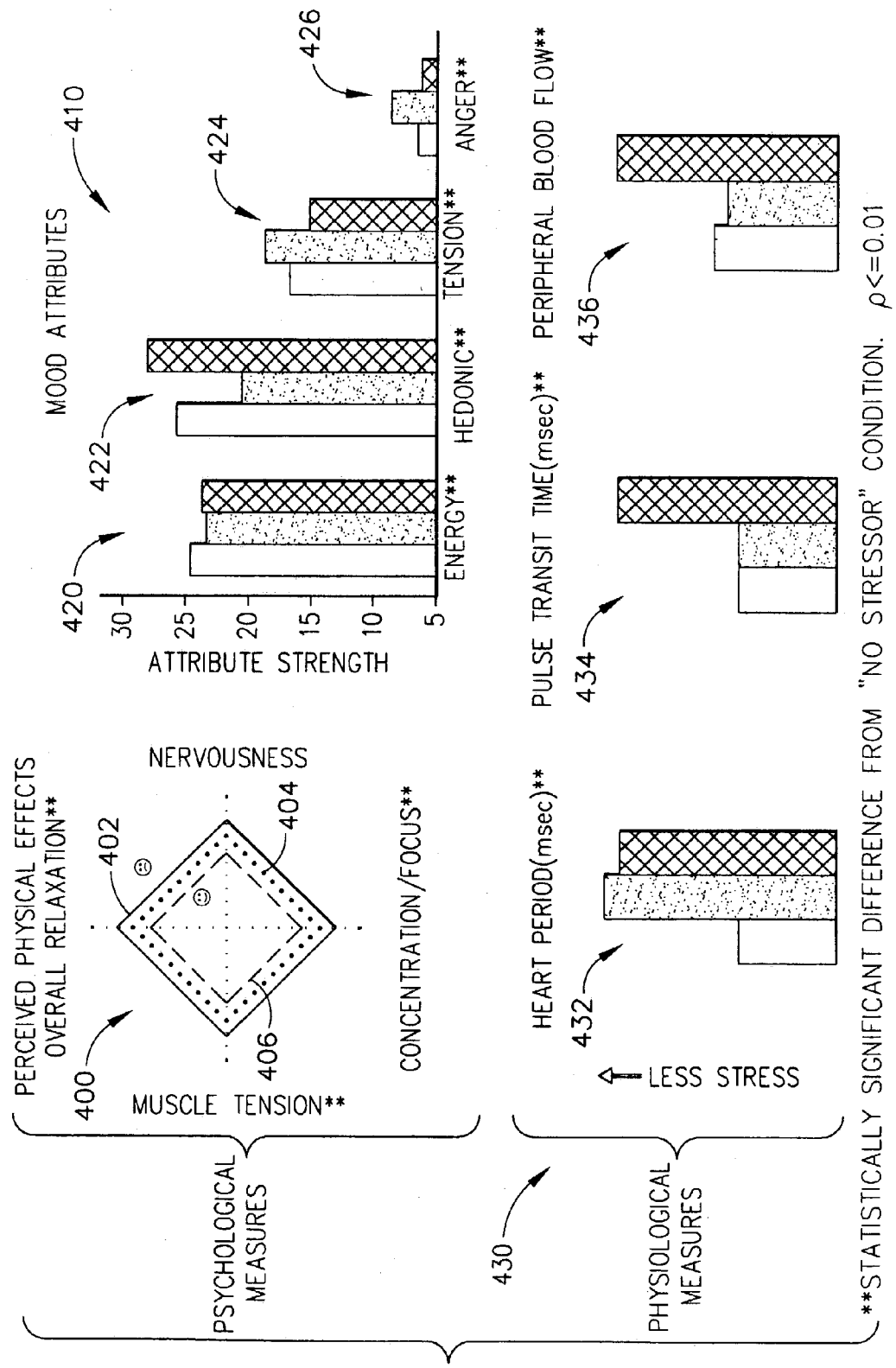
FIG. 12 is a bar chart and diamond chart of psychological and physiological components of the results obtained on a test subject using the procedure of FIG. 4.

FIG. 12 illustrates a further example of perceived physical effects and mood attributes with regard to psychological measures, as well as depicting certain physiological measures. A "diamond chart" 400 illustrates the perceived physical results for overall relaxation, muscle tension, nervousness, and concentration or "focus." The outermost diamond 402 represents a person's psychological state during an emotional stressor event, while the innermost diamond 406 represents the person's psychological perceived physical effects when no stressor is involved. The middle diamond 404 represents a cognitive stressor event.

The diamond chart 400 could instead be represented by four sets of bar graphs, if desired. The mood attributes chart 410 is illustrated as a bar graph, and represents energy at 420, hedonic at 422, tension at 424, and anger at 426. Each mood attribute has three bars, in which the left-most bar represents a cognitive stressor event, the middle-most bar (which is dotted) represents the emotional stressor contribution, while the right-most bar (which is cross-hatched) represents no stressor condition. It should be noted that the first two mood attributes (i.e., energy and hedonic) are quantified such that the larger or higher the bar, the better for the person. On the other hand, for the second two attributes of tension and anger, the lower the height of the bar, the better for the person. (This is one good reason to not represent these attributes on a "diamond" chart.)

The physiological measures are represented in the bar chart 430 for heart period (at 432), pulse transit time (at 434), and peripheral blood flow (at 436). For all three bar charts in the graph 430, the higher the bar, the less stress the person is undergoing.

Figure 13:
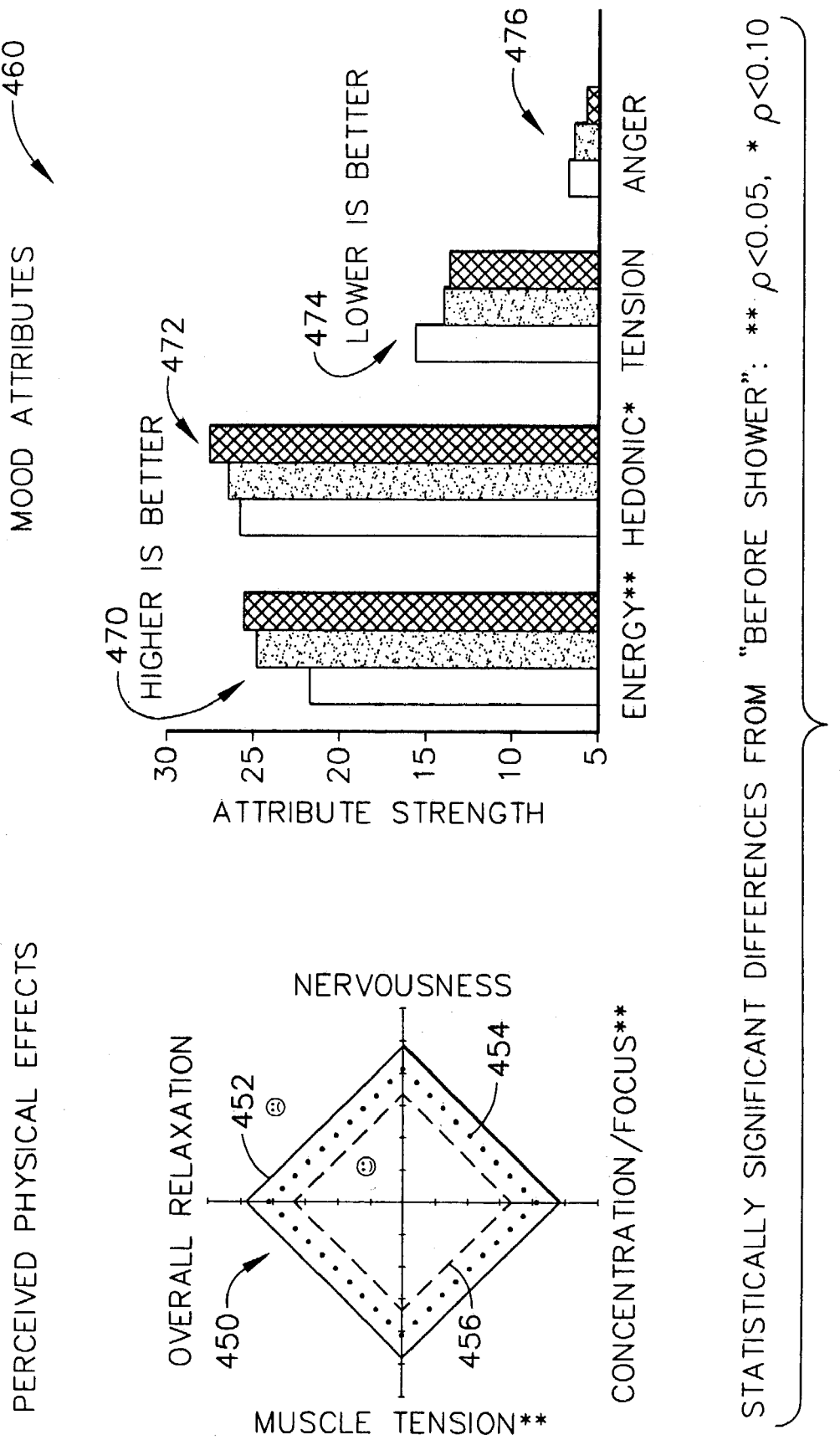
FIG. 13 is a diamond chart and a bar chart of the results obtained of a test subject using the procedure of FIG. 4, including results obtained when a fragrance or aroma has been introduced.

FIG. 13 illustrates the perceived physical effects and mood attributes for a test subject undergoing an activity, with or without a fragrance or aroma being introduced. The "diamond chart" 450 shows the perceived physical effects for overall relaxation, muscle tension, nervousness, and concentration/focus. The outermost diamond 452 represents the person's perceived physical effects before the task or activity occurs. The mid-interior diamond shape 454 represents the perceived physical effects of the test subject after completing the task or activity, which was a relaxing activity. The innermost diamond at 456 represents the perceived physical effects for the person after completing the relaxing activity while a fragrance or aroma was introduced. As can be seen from the chart 450, both the activity/task and the aroma/fragrance introduced a certain measure of relaxation.

As with FIG. 12, the diamond chart 450 could have been represented by four individual bar charts, each having three bars to show the perceived physical effects.

A bar chart 460 represents mood attributes for energy at 470, hedonic at 472, tension at 474, and anger at 476. Again, as discussed in reference to FIG. 12, the first two attributes 470 and 472 are such that the larger or higher the bar, the better for the person, while the second two attributes 474 and 476 are such that the lower the bar, the better for the person.

The left-most bar in each chart represents the person's mood attribute before the relaxing activity has occurred. The middle bar, which is dotted, represents the person's mood attribute after completing the relaxing task or activity (such as taking a shower or having hot towels applied to their skin). The right-most bar represents the person's mood attributes after completing both the relaxing activity/task and while having a fragrance/aroma introduced. As can be seen from the data, the right-most bar shows the best result in this instance.

The graphical data illustrated in FIGS. 10–13 are representative of the type of output that can be achieved using the computer test setup of the PC 100 with the input sensors and the olfactometer 160, used to test or measure a person's psychological and physiological components of acute stress. This instrumented system and methodology of the present invention can provide a much more scientifically accurate measure of a person's acute stress level by analyzing the psychological effects as well as the physiological effects during the testing procedures. Not only can the present invention methodology evaluate the introduction of a flavor or fragrance, but also can analyze the effect on a person (the test subject) of a task or activity, whether that task/activity is relaxing or the opposite.

With regard to fragrances, aromas, or flavors, such fragrances/aromas/flavors can be provided in products sold by manufacturers, in which such products could have a therapeutic beneficial effect on most people. Of course, certain fragrances/aromas/flavors found in products may affect some people to a greater extent than other such products, however, the methodology of the present invention can easily obtain a statistical analysis as to the percentage of population that would be beneficially affected by these products. Moreover, certain fragrances can be used in combination to provide not only a pleasing smell, for example, but also have beneficial psychological/physiological effects on a person. In instances where the main fragrance (that has a beneficial effect on a person's acute stress level) is less than desirable as a pure "smell," then that particular fragrance can be masked by other oils, for example, to provide an overall smell/fragrance that is pleasing. Again, the methodology and hardware provided by the present invention can assist in evaluating such mixtures of fragrances/oils/flavors that could be used in a useful product. Furthermore, the methodology and hardware can evaluate "relaxing" tasks, or the benefit (if any) of medical or therapeutic devices on a person.

It will be also understood that fragrance concentration of an aroma compound or product can be of importance on a person's stress. For example, at low concentration, lavender relaxes (at 1% and less); however, at 10% concentration it is stimulating. The importance of concentration must be recognized, as it may be at least as important as the ratio of ingredients of a mixture.

It will be understood that the logical operations described in relation to the flow chart of FIG. 2 can be implemented using sequential logic, such as by using microprocessor technology, or using a logic state machine, or perhaps by discrete logic; it even could be implemented using parallel processors. The preferred embodiment uses a microprocessor (e.g., microprocessor 110) to execute software instructions that are stored in memory cells within ROM 112 or RAM 114. Of course, other circuitry could be used to implement these logical operations depicted in FIG. 2 without departing from the principles of the present invention.

It will be further understood that the precise logical operations depicted in the flow chart of FIG. 2 and testing diagram of FIG. 4 and discussed hereinabove, could be somewhat modified to perform similar, although not exact, functions without departing from the principles of the present invention. The exact nature of some of the decision steps and other commands in these flow charts are directed toward a specific exemplary testing procedure as described above, and certainly similar, but somewhat different, steps could be used with other hardware setups, or with other instrument or sensing software, or by use of other questionnaires, for example, with the overall inventive results being the same.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described in order to best illustrate the principles of the invention and its practical application to thereby enable one of ordinary skill in the art to best utilize the invention in various embodiments and with various modifications as are suited to the particular use contemplated. It is intended that the scope of the invention be defined by the claims appended hereto.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for evaluating acute stress of a person, said method comprising:
(a) providing a computerized apparatus having a memory circuit for storage of data, an interface circuit, a processing circuit, and at least one sensing device that is in communication with said interface circuit, wherein said at least one sensing device is used to detect at least one physiological parameter of a test subject;
(b) initiating a first stress interval, during which said test subject performs at least one predetermined task designed to induce some acute stress;
(c) initiating a first questionnaire interval, during which said test subject answers questions designed to evaluate at least one psychological component of acute stress;
(d) initiating a first relaxation interval, during which said test subject is allowed to relax;
(e) initiating a second questionnaire interval, during which said test subject answers questions designed to evaluate at least one psychological component of acute stress;
(f) initiating a second stress interval, during which said test subject performs at least one predetermined task designed to induce some acute stress; and
(g) initiating a third questionnaire interval, during which said test subject answers questions designed to evaluate at least one psychological component of acute stress;
wherein a stimulus may be introduced into said test subject's environment during at least one of: (i) said first stress interval, (ii) said first relaxation interval, and (iii) said second stress interval.

2. The method as recited in claim 1, wherein: said stimulus comprises one of: (a) a fragrance, (b) a flavor, (c) a task, and (d) a product.

3. The method as recited in claim 2, wherein: (a) said fragrance is in one of: a solid form, a liquid form, and a gaseous form; (b) said flavor is in one of: a solid form, a liquid form, and a gaseous form; (c) said task comprises an activity that may tend to either decrease acute stress or increase acute stress; and (d) said product is one of: a liquid fragrance, a gaseous odor, a medical device, and a therapeutic device.

4. The method as recited in claim 1, wherein: said stimulus is not introduced in one of the first and second stress intervals, thereby evaluating a stimulus that was introduced in the other of the first and second stress intervals.

5. The method as recited in claim 1, wherein: no stimulus is introduced during said first relaxation interval.

6. The method as recited in claim 1, wherein: a questionnaire is used during at least one of said questionnaire intervals, and said test subject answers questions from the questionnaire that are designed to evaluate at least one psychological component of acute stress.

7. The method as recited in claim 6, wherein: said questionnaire comprises a plurality of quick-answer questions that provide a measure of perceived physiological effects of acute stress.

8. The method as recited in claim 7, wherein: answers to said quick-answer questions provide a measure of the test subjects' psychological state.

9. The method as recited in claim 1, further comprising: an initial baseline interval, followed by a chronic stress questionnaire, before entering said first stress interval.

10. The method as recited in claim 9, wherein during the baseline interval, said at least one sensing device is placed on the test subject, and then tested for proper operation.

11. The method as recited in claim 1, further comprising: a plurality of further stress intervals and relaxation intervals, each of said intervals being followed by a further questionnaire intervals.

12. The method as recited in claim 1, wherein said at least one sensing device is a non-invasive device.

13. The method as recited in claim 12, wherein said at least one sensing device comprises at least one of: a blood volume pulse (BVP) sensor, and an EKG sensor.

14. The method as recited in claim 12, wherein said at least one sensing device is used to generate data on at least one of: heart period, pulse transit time, peripheral blood flow, and standard deviation of normal to normal beats (SDNN).

15. The method as recited in claim 6, wherein said questionnaire is used to generate data on predetermined psychological parameters including at least one of: energy, hedonic, tension, anger, overall relaxation, muscle tension, nervousness, and concentration/focus.

16. The method as recited in claim 15, wherein said predetermined psychological parameters are analyzed to generate at least one of: a personal stress profile; and a delta chart of stress vs. relaxation effects.

* * * * *

UNITED STATES PATENT AND TRADEMARK OFFICE
CERTIFICATE OF CORRECTION

PATENT NO. : 7,213,600 B2 Page 1 of 1
APPLICATION NO. : 10/405378
DATED : May 8, 2007
INVENTOR(S) : Magda El-Nokaly et al.

It is certified that error appears in the above-identified patent and that said Letters Patent is hereby corrected as shown below:

Page 2 of Title page, Column 1

Line 5 of the text, delete "conputations" and insert -- computations --.

Column 20

Line 49, delete "Std" over the word "Mean" in the heading of Table #7.

Line 49, insert -- Std -- over the word "Error" in the heading of Table #7.

Column 21

Line 58, after "α", insert an equal sign -- = --.

Signed and Sealed this

Twenty-first Day of August, 2007

JON W. DUDAS
*Director of the United States Patent and Trademark Office*